US 6,370,478 B1

(12) United States Patent
Stoughton et al.

(10) Patent No.: US 6,370,478 B1
(45) Date of Patent: Apr. 9, 2002

(54) METHODS FOR DRUG INTERACTION PREDICTION USING BIOLOGICAL RESPONSE PROFILES

(75) Inventors: Roland Stoughton, San Diego, CA (US); Sergey Stepaniants, Kirkland, WA (US)

(73) Assignee: Rosetta Inpharmatics, Inc., Kirkland, WA (US)

( * ) Notice: Subject to any disclaimer, the term of this patent is extended or adjusted under 35 U.S.C. 154(b) by 0 days.

(21) Appl. No.: 09/222,595

(22) Filed: Dec. 28, 1998

(51) Int. Cl.$^7$ ............... G01N 33/48; G01N 33/53; C12Q 1/68; A01N 37/18; A01N 43/04
(52) U.S. Cl. ............... 702/19; 435/6; 435/7.1; 435/7.2; 436/501; 436/63; 514/2; 514/44
(58) Field of Search ............... 514/2, 44; 435/6, 435/7.1, 7.2; 436/501, 63; 702/19

(56) References Cited

U.S. PATENT DOCUMENTS

| | | | |
|---|---|---|---|
| 4,946,778 A | | 8/1990 | Ladner et al. |
| 5,300,425 A | * | 4/1994 | Kauwar ............ 435/7.9 |
| 5,445,934 A | | 8/1995 | Fodor et al. |
| 5,510,270 A | | 4/1996 | Fodor et al. |
| 5,539,083 A | | 7/1996 | Cook et al. |
| 5,541,070 A | * | 7/1996 | Kauwar ............ 435/7.9 |
| 5,556,752 A | | 9/1996 | Lockhart et al. |
| 5,564,433 A | | 10/1996 | Thornton |
| 5,569,588 A | | 10/1996 | Ashby et al. |
| 5,578,832 A | | 11/1996 | Trulson et al. |
| 5,645,988 A | | 7/1997 | Vande Woude et al. |
| 5,744,305 A | | 4/1998 | Fodor et al. |
| 5,769,074 A | * | 6/1998 | Barnhill et al. ............ 128/630 |
| 5,777,888 A | | 7/1998 | Rine et al. |
| 5,800,992 A | | 9/1998 | Fodor et al. |
| 5,811,231 A | | 9/1998 | Farr et al. |

FOREIGN PATENT DOCUMENTS

| | | |
|---|---|---|
| EP | 0 534 858 A1 | 9/1992 |
| EP | 0 816 511 A1 | 1/1996 |
| WO | WO 88/09810 | 12/1988 |
| WO | WO 90/11364 | 10/1990 |
| WO | WO 94/17208 | 8/1994 |
| WO | WO 97/10365 | 3/1997 |
| WO | WO 97/27317 | 7/1997 |
| WO | WO 98/06874 | 2/1998 |
| WO | WO 99/58720 | 11/1999 |

OTHER PUBLICATIONS

Lin et al., Biochimica et Biopysica Seta, vol. 1082, pp. 177–184, 1991.*
Blanchard et al., 1996, "High–density oligonucleotide arrays," *Biosensors & Bioelectronics* 11:687–690.
Blanchard et al., 1996, "Sequence to array: Probing the genome's secrets," *Nature Biotechnology* 14:1649.
Bryant et al., (1998), "Gene Expression and Genetic Networks," *Pacific Symposium on Biocomputing* 3:3–5. Available Web Site: http://www–smi.stanford.edu/projects/helix/psb98/Accessed on: Nov. 24, 1998 3:48 p.m.
Bulmer, *Principles of Statistics*, Dover, N.Y., 1967, pp. 117, 221–224.

(List continued on next page.)

*Primary Examiner*—Ardin H. Marschel
(74) *Attorney, Agent, or Firm*—Pennie & Edmonds LLP

(57) ABSTRACT

This invention provides methods for detecting and predicting drug interaction. In one embodiment of the invention, a plurality of cellular constituents in a biological sample is monitored as the sample is subject to various drug treatments. The response of the cellular constituents are analyzed to detect interactions. This method is particularly useful for predicting drug interaction using a model organism. It is also useful for analyzing interaction between any perturbations to a biological system.

44 Claims, 7 Drawing Sheets

*If a member of the overlap signature

OTHER PUBLICATIONS

Carr et al., 1997, "Templates for Looking at Gene Expression Clustering," *Statistical Computing & Statistical Graphics Newsletter* pp. 20–29.

Chee et al., 1996, "Accessing genetic information with high–density DNA arrays," *Science* 274:610–614.

D'haeseleer et al., (1998), "Mining the Gene Expression Matrix: Inferring Gene Relationships From Large Scale Gene Expression Data" Available Web Site: www.cs.unm.edu/~patrik/networks/IPCAT/ipcat.html.

DeRisi et al., 1996, "Use of a cDNA microarray to analyze gene expression patterns in human cancer," *Nature Genetics* 14:457–460.

DeRisi et al., 1997, "Exploring the Metabolic and Genetic Control of Gene Expression on a Genomic Scale," *Science* 278:680–686.

Eisen et al., 1998, "Cluster analysis and display of genome–wide expression patterns", Proc. Natl. Acvad. Sci. USA 95:14863–14868.

Esposito et al., 1985, "Orthopoxvirus DNA: A Comparison of Restriction Profiles and Maps" Virology 143:230–251.

Fingl et al., 1975, In: *The Pharmacological Basis of Therapeutics*, Ch. 1, p. 1.

Fodor et al., 1991, "Light–directed spatially addressable parallel chemical synthesis," Science 251:767–773.

Fuhrman et al., (1997), "Genetic Network Inference," *Proceedings of the International Conference on Complex Systems*, Nashua, NH, 21–26. Available Web Site: http://rsb.info.nih.gov/mol–physiol/ICCS/inference/ICCS.html Accessed on: Nov. 18, 1998 6:14 p.m.

Glaser, "Experts gather to discuss technologies being developed for functional genomic analysis," *Genetic Engineering News* vol. 16, Nov. 15, 1996.

Goffeau et al., 1996, "Life with 6000 genes," *Science* 274:546–567.

Herskowitz, 1987, "Functional inactivation of genes by dominant negative mutations," *Nature* 329:219–222.

Lennon and Lehrach, 1991, "Hybridization analyses of arrayed cDNA libraries" *Trends Genet.* 7:314–317.

Lockhart et al., 1996, Expression monitoring by hybridization to high–density oligonucleotide arrays, *Nature Biotechnology* 14:1675–1680.

Marnellos et al., (1998) "A Gene Network Approach to Modeling Early Neurogenesis in Drosophila," *Pacific Symposium on Biocomputing* 3:30–41. Available Web Site: http://www–smi.stanford.edu/projects/helix/psb98/ Accessed on: Nov. 24, 1998 3:48 p.m.

Michaels et al., (1998), "Cluster Analysis and Data Visualization of Large–Scale Gene Expression Data," *Pacific Symposium on Biocomputing* 3:42–53. Available Web Site: http://www–smi.stanford.edu/projects/helix/psb98/ Accessed on: Nov. 24, 1998 3:48 p.m.

Nguyen et al., 1995, "Differential gene expression in the murine thymus assayed by quantitative hybridization of arrayed cDNA clones," *Genomics* 29:207–216.

Sanger et al., 1996, "Comparison of the Pharmacological Profiles of the Hypnotic Drugs, zaleplon and zolpidem" Euro. J. Pharm. 313:35–42.

Thomas et al., 1995, "Dynamical behaviour of biological regulatory networks—I. Biological role of feedback loops and practical use of the concept of the loop–characteristic state," *Bull. Math. Biol.* 57:247–276.

Weinstein et al., (1997), "An Information–Intensive Approach to the Molecular Pharmacology of Cancer," *Science* 275:343–349.

Wen et al., (1998), "Large–Scale Temporal Gene Expression Mapping of Central Nervous System Development," *Proc. Natl. Acad. Sci. USA* 95:334–339.

Yatscoff, R.W. et al., 1996, "Pharmacodynamic Monitoring of Immunosuppressive Drugs," *Transplantation Proceedings* 28:3013–3015.

Zhao et al., 1995, "High–density cDNA filter analysis: a novel approach for large–scale, quantitative analysis of gene expression," *Gene* 156:207–213.

Okada et al., 1996, Biochem. J. 317:475–480.

\* cited by examiner

*If a member of the overlap signature

METHODS FOR DRUG INTERACTION PREDICTION USING BIOLOGICAL RESPONSE PROFILES

1. FIELD OF INVENTION

The present invention is related to drug discovery. Specifically, this invention provides methods useful for predicting drug interactions based upon the interaction between biological response profiles. The methods of the invention is also useful for analyzing the interaction between any perturbations to a biological system.

2. BACKGROUND OF INVENTION

Simultaneous administration of several drugs, or combination therapy, is often necessary to achieve desired therapeutic objectives. For example, a heart failure patient may be treated with a diuretic in conjunction with a vasodilator and/or a cardiac glucoside so that the patient will have adequate cardiac output, but free from edema. In cancer chemotherapy or antimicrobial therapy, drug combination is desired to delay the emergence of drug resistant tumor cells or microorganisms. Nies, 1990, Principles of Therapeutics, In (Goodman and Gilman eds.) THE PHARMACOLOGICAL BASIS OF THERAPEUTICS. Recently, combination therapy has been successfully used in anti-viral therapies, such as in the suppression of replication of Human Immunodeficiency Virus (HIV).

Drug combination, while offering many benefits, often causes unintended adverse reactions because of undesirable drug interactions. Drug interaction is the ability of one drug to alter the effects of another. It may be beneficial or detrimental. See, http://des.sw.cc.va.us/nursing/DrugInter.html (accessed on Nov. 13, 1998). As an example of beneficial drug interaction effect, the combination of Demerol and Vistaril enhances the sedative effect of Demerol. Id. The combination of Aspirin and Coumadin, however, is detrimental because Coumadin increases the possibility of Aspirin induced bleeding. Id.

It is estimated that the incidence of drug interaction ranges from 3–40% in patients under combination therapy. Nies, 1990, Principles of Therapeutics, In (Goodman and Gilman eds.) THE PHARMACOLOGICAL BASIS OF THERAPEUTICS; Naguib et al., 1997, *Clinically Significant Drug Interactions with General Anesthetics-incidence, Mechanisms and Management,* MIDDLE EAST J. ANESTHESIOL,. 14:127–183. The frequency of drug interaction increases disproportionally with the increase in the number of drugs in combination. For example, only 5% of patients with fewer than six drugs manifested clinical signs of drug interaction; while 40% of patients given 16 drugs experienced an adverse drug interaction. Naguib et al.

Because most hospital patients receive at least six drugs in combination, drug interactions are of serious clinical concern. The problem of drug interaction is worsened by the growing population of geriatric patients who are often prescribed multiple medications for concomitant medical illnesses and who often have diminished capacity to metabolize drugs. Id. In fact, drug interactions have become the frequent causes of treatment failure and adverse reactions. Anastasio, et al., 1997, *Drug Interactions: Keeping It Straight.,* AM. FAMILY PHYSICIAN 56:883. Steel et al., 1981, *Iatrogenic Illness on a General Medical Service at a University Hospital.* N. ENGL. J. MED. 304:638–642.

Because of the important clinical consequences of drug interactions, it is desirable to predict potential interactions of a drug candidate with other drugs or drug candidates in the early phase of drug development. Unfortunately, the ability to predict potentially dangerous interactions between drug treatments is lacking. Even at the late stage of drug development, such as at the stage of clinical trials, drug interactions are still particularly difficult to investigate because of the number of combinations that would have to be tested.

Discussion or citation of a reference herein shall not be construed as an admission that such reference is prior art to the present invention.

3. SUMMARY OF THE INVENTION

Accordingly, this invention provides methods suitable for predicting potential drug interaction in the early stage of drug development.

In one aspect of the invention, a plurality of cellular constituents (measurable biological variables, such as mRNA, proteins, etc., defined infra) are measured while a biological sample (either a model organism or a target subject) is separately subjected to the application of a perturbation A (such as a drug A) and a perturbation B (such as a drug B). The change in those cellular constituents (response of cellular constituents) are calculated, preferably as the log ratio of cellular constituent levels before and after treatment with either perturbation A or perturbation B.

A substantial overlap between the response of cellular constituents to perturbations A and B suggests that the two drugs will have a potential overlapping effect in vivo.

In preferred embodiments, the cellular constituents are mRNA transcripts. Perturbation interaction (such as drug interaction) is tested in a model organism such as a yeast culture.

In another aspect of the invention, a biological sample is subjected to the treatment of perturbation A (such as a drug A). The response ($R_A$) of a number of cellular constituents is calculated based upon the level of cellular constituents before (baseline) and after treatment with perturbation A. The biological sample is then treated with perturbation A in the presence of perturbation B (such as a drug B). The response ($R_{A|B}$) of the cellular constituents is calculated based upon the level of cellular constituents before (perturbation B only) and after (perturbations A and B) treatment with perturbation A.

The response profile $R_A$ is plotted against response profile $R_{A|B}$ with response of each cellular constituent as a data point. One axis represents response to drug A and another axis represents response to perturbation A in the presence of perturbation B. In one preferred embodiment, $R_{A|B}$ is plotted along a vertical axis and $R_A$ is plotted along a horizontal axis. In this embodiment, if a cellular constituent falls along the 45° line, the activity of perturbation A on the cellular constituent is predicted to be independent of perturbation B. If a cellular constituent falls within the upper left or lower right quadrants, the activity of perturbation A on the cellular constituent is predicted to be dependent upon perturbation B. If a cellular constituent falls within the lower left or upper right quadrant, but not along the 45° line, the activity of perturbation A on the cellular constituent is predicted to be either reduced or enhanced by perturbation B.

In some embodiments, the membership in the different regions is assigned with an objective statistical significance. The statistical significance is calculated based upon the error associated with each cellular constituent response measurement. In some instances, the error is derived from the variation between repeated measurements. In some other instances, the error is estimated based upon other error models.

In some other embodiments, interaction between perturbation A (such as a drug A) and perturbation B (such as a drug B) is calculated according to: $\{I\}=\{R_{A,B}\}-(\{R_A\}+\{R_B\})$. Vector $\{I\}$ is the interaction effect. Vector $\{R_A\}$ represents a set of cellular constituents with threshold crossing response when treating with perturbation A. Vector $\{R_B\}$ represents a set of cellular constituents with threshold crossing response when treating with perturbation B. Vector $\{R_{A,B}\}$ is a set of cellular constituents with threshold crossing response when treating with both perturbations A and B.

In yet another aspect of the invention, the methods of the invention are applied to analyze the interactions among any number of perturbations (such as any number of drugs). In some embodiments, the interaction between two groups of perturbations (groups A and B) are analyzed using the methods of the invention. In such embodiments, the response to group A is monitored as $R_A$; the response to group B is the $R_B$; and the response to group A in the presence of group B is $R_{A|B}$.

4. BRIEF DESCRIPTION OF THE FIGURES

5. DETAILED DESCRIPTION OF THE INVENTION

Figure 1:
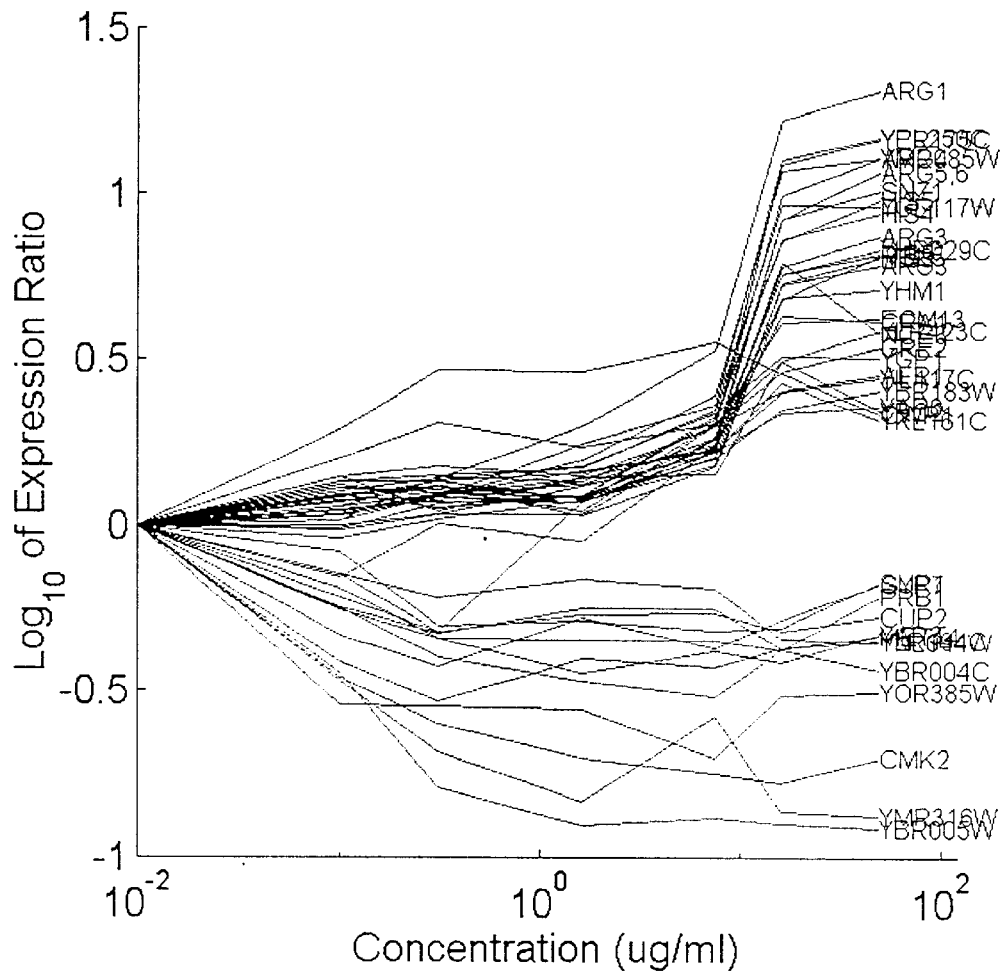
FIG. 1 shows the response of various genes to increasing concentration of FK506.

This section presents a detailed description of the invention and its applications. This description is by way of several exemplary illustrations, in increasing detail and specificity, of the general methods of this invention. These examples are non-limiting, and related variants will be apparent to one of skill in the art.

Although, for simplicity, this disclosure often makes references to gene expression profiles, transcriptional rate, transcript levels, etc., it will be understood by those skilled in the art that the methods of the inventions are useful for the analysis of any biological response profile and their interactions. In particular, one skilled in the art will recognize that the methods of the present invention are equally applicable to biological profiles which comprise measurements of other cellular constituents such as, but not limited to, measurements of protein abundance or protein activity levels.

The description of the invention, for simplicity, is largely in terms of interactions among any number of different "drugs." However, the methods of the invention is also applicable, as will be apparent to one skilled in the art, to the analysis of interactions between any two or more perturbations to a biological sample.

5.1. Introduction

This section presents a background about representations of biological state and biological responses in terms of cellular constituents, drugs and drug interactions.

5.1.1. Definition of Biological State

As used in herein, the term "biological sample" is broadly defined to include any cell, tissue, organ or multicellular organism. A biological sample can be derived, for example, from cell or tissue cultures in vitro. Alternatively, a biological sample can be derived from a living organism or from a population of single cell organisms.

The state of a biological sample can be measured by the content, activities or structures of its cellular constituents. The state of a biological sample, as used herein, is taken from the state of a collection of cellular constituents, which are sufficient to characterize the cell or organism for an intended purpose including, but not limited to characterizing the effects of a drug or disease or other perturbation. The term "cellular constituent" is also broadly defined in this disclosure to encompass any kind of measurable biological variable. The measurements and/or observations made on the state of these constituents can be of their abundances (i.e., amounts or concentrations in a biological sample), or their activities, or their states of modification (e.g., phosphorylation), or other measurements relevant to the biology of a biological sample. In various embodiments, this invention includes making such measurements and/or observations on different collections of cellular constituents. These different collections of cellular constituents are also called herein aspects of the biological state of a biological sample.

One aspect of the biological state of a biological sample (e.g., a cell or cell culture) usefully measured in the present invention is its transcriptional state. In fact, the transcriptional state is the currently preferred aspect of the biological state measured in this invention. The transcriptional state of a biological sample includes the identities and abundances of the constituent RNA species, especially mRNAs, in the cell under a given set of conditions. Preferably, a substantial fraction of all constituent RNA species in the biological sample are measured, but at least a sufficient fraction is measured to characterize the action of a drug or other perturbation of interest. The transcriptional state of a biological sample can be conveniently determined by, e.g., measuring cDNA abundances by any of several existing gene expression technologies. One particularly preferred embodiment of the invention employs DNA arrays for measuring mRNA or transcript level of a large number of genes.

Another aspect of the biological state of a biological sample usefully measured in the present invention is its translational state. The translational state of a biological sample includes the identities and abundances of the constituent protein species in the biological sample under a given set of conditions. Preferably, a substantial fraction of all constituent protein species in the biological sample is measured, but at least a sufficient fraction is measured to characterize the action of a drug of interest. As is known to those of skill in the art, the transcriptional state is often representative of the translational state.

Other aspects of the biological state of a biological sample are also of use in this invention. For example, the activity state of a biological sample, as that term is used herein, includes the activities of the constituent protein species (and also optionally catalytically active nucleic acid species) in the biological sample under a given set of conditions. As is known to those of skill in the art, the translational state is often representative of the activity state.

This invention is also adaptable, where relevant, to "mixed" aspects of the biological state of a biological sample in which measurements of different aspects of the biological state of a biological sample are combined. For example, in one mixed aspect, the abundances of certain RNA species and of certain protein species, are combined with measurements of the activities of certain other protein species. Further, it will be appreciated from the following that this invention is also adaptable to other aspects of the biological state of the biological sample that are measurable.

The biological state of a biological sample (e.g., a cell or cell culture) is represented by a profile of some number of cellular constituents. Such a profile of cellular constituents can be represented by the vector S.

$$S=[S_1, \ldots S_i, \ldots S_k] \quad (1)$$

Where $S_i$ is the level of the i'th cellular constituent, for example, the transcript level of gene i, or alternatively, the abundance or activity level of protein i.

In some embodiments, cellular constituents are measured as continuous variables. For example, transcriptional rates are typically measured as number of molecules synthesized per unit of time. Transcriptional rate may also be measured as percentage of a control rate. However, in some other embodiments, cellular constituents may be measured as categorical variables. For example, transcriptional rates may be measured as either "on" or "off", where the value "on" indicates a transcriptional rate above a predetermined threshold and value "off" indicates a transcriptional rate below that threshold.

5.1.2. Representation of Biological Responses

The responses of a biological sample to a perturbation, such as the application of a drug, can be measured by observing the changes in the biological state of the biological sample. A response profile is a collection of changes of cellular constituents. In the present invention, the response profile of a biological sample (e.g., a cell or cell culture) to the perturbation m is defined as the vector $R^{(m)}$:

$$R^{(m)}=[R_1^{(m)}, \ldots R_i^{(m)}, \ldots R_k^{(m)}] \quad (2)$$

Where $R_i^m$ is the amplitude of response of cellular constituent i under the perturbation m. In some particularly preferred embodiments of this invention, the biological response to the application of a drug, a drug candidate or any other perturbation, is measured by the induced change in the transcript level of at least 2 genes, preferably more than 10 genes, more preferably more than 100 genes and most preferably more than 1,000 genes.

In some embodiments of the invention, the response is simply the difference between biological variables before and after perturbation. In some preferred embodiments, the response is defined as the ratio of cellular constituents before and after a perturbation is applied.

In some preferred embodiments, $R_i^m$ is set to zero if the response of gene i is below some threshold amplitude or confidence level determined from knowledge of the measurement error behavior. In such embodiments, those cellular constituents whose measured responses are lower than the threshold are given the response value of zero, whereas those cellular constituents whose measured responses are greater than the threshold retain their measured response values. This truncation of the response vector is a good strategy when most of the smaller responses are expected to be greatly dominated by measurement error. After the truncation, the response vector $R^{(m)}$ also approximates a 'matched detector' (see, e.g., Van Trees, 1968, *Detection, Estimation and Modulation Theory Vol. I*, Wiley & Sons) for the existence of similar perturbations. It is apparent to those skilled in the art that the truncation levels can be set based upon the purpose of detection and the measurement errors. For example, in some embodiments, genes whose transcript level changes are lower than two fold or more preferably four fold are given the response value of zero.

More preferably, the response profiles are expressed as the logarithm of the ratio of values of cellular constituents before and after the application of a perturbation. Each cellular constituent yields one ratio in an experiment condition pair (with and without the application of a particular perturbation). Therefore:

$$R_i^{(m)} = \log_{10}\left(\frac{S_i^{(m)}}{S_i^{(o)}}\right) \quad (3)$$

where $S^{(m)}_i$ is value of cellular constituent i under perturbation m; $S^{(o)}$ is the value of cellular constituent i without perturbation. Usually, the logarithms of ratios are most appropriate for some biological variables where fold changes are more biologically relevant than absolute level changes, because the log(ratio) gives equal increments for equal fold changes.

In some preferred embodiments, perturbations are applied at several levels of strength. For example, different amounts of a drug may be applied to a biological sample to observe its response. In such embodiments, the perturbation responses may be interpolated by approximating each by a single parameterized "model" function of the perturbation strength u. An exemplary model function appropriate for approximating transcriptional state data is the Hill function, which has adjustable parameters a, $u_0$, and n.

$$H(u) = \frac{a(u/u_0)^n}{1 + (u/u_0)^n} \quad (4)$$

The adjustable parameters are selected independently for each cellular constituent of the perturbation response. Preferably, the adjustable parameters are selected for each cellular constituent so that the sum of the squares of the differences between the model function (e.g., the Hill function, Equation 4) and the corresponding experimental data at each perturbation strength is minimized. This preferable parameter adjustment method is well known in the art as a least squares fit. Other possible model functions are based on polynomial fitting, for example by various known classes of polynomials. More detailed description of model fitting and biological response has been disclosed in Friend and Stoughton, Methods of Determining Protein Activity Levels Using Gene Expression Profiles, U.S. Provisional Application Ser. No. 60/084,742, filed on May 8, 1998, which is incorporated herein by reference for all purposes.

5.1.3. Cellular Constituent Sets

In some instances, the biological state of a cell may be represented in terms of co-varying cellular constituent sets. Methods for defining co-varying cellular constituent sets are described in, for example, Roland Stoughton and Yudong He, "Methods for Using Co-Regulated Genesets to Enhance Detection and Classification of Gene Expression Patterns," U.S. patent application Ser. No. 09/220,275, filed on Dec. 23, 1998, which is a continuation-in-part of U.S. patent application Ser. No. 09/179,569, filed on Oct. 27, 1998; both applications are incorporated herein by reference for all purposes. For example, in a particular embodiment, a biological sample (or a population of biological samples) is subjected to a wide variety of perturbations. The biological sample is monitored for their cellular constituents (level, activity, or structure change, etc.). The responses of cellular constituents to various perturbations are analyzed to generate co-varying sets. The data are first grouped by cluster analysis to generate a cluster tree which depicts the similarity of the responses of cellular constituents to perturbation. Cellular constituents within a defined branch are classified as a cellular constituent set. Biological state and biological responses of a biological sample are represented by combined values for cellular constituent sets.

Using set values does not necessarily cause loss of information by combining individual cellular constituent values. Because the cellular constituents within a set co-vary, individual cellular constituents provides little more information than the combined set value. In most embodiments, in this step, the quantitative description of a profile changes from a list of, for example, 100 numbers to a substantially shorter list, for example 10, representing the amplitude of each individual response pattern (coordinated change in any one geneset) needed to closely represent, in a sum, the entire profile.

5.1.4. Drug Action and Biological Pathways

Drugs, as defined herein, are any compounds of any degree of complexity that perturb a biological system, whether by known or unknown mechanisms, whether or not they are used therapeutically, and whether or not their effects are beneficial (e.g., therapeutic) or toxic to a biological system. Drugs thus include: typical small molecules of research or therapeutic interest; naturally-occurring factors, such as endocrine, paracrine, or autocrine factors or factors interacting with cell receptors of all types; intracellular factors, such as elements of intracellular signaling pathways; factors isolated from other natural sources; and so forth. The biological effect of a drug may be a consequence of, inter alia, drug-mediated changes in the rate of transcription or degradation of one or more species of RNA, the rate or extent of translation or post-translational processing of one or more polypeptides, the rate or extent of the degradation of one or more proteins, the inhibition or stimulation of the action or activity of one or more proteins, and so forth. In fact, most drugs exert their affects by interacting with a protein. Drugs that increase rates or stimulate activities of a protein are called herein "activating drugs," while drugs that decrease rates or inhibit activities of a protein are called herein "inhibiting drugs."

Drug effects on a cell, whether therapeutic or toxic and however measured in a particular implementation, are generally represented by combining the effects of the drug on individual pathways. As used herein, a biological pathway is generally understood to be a collection of cellular constituents related in that each cellular constituent of the collection is influenced according to some biological mechanism by one or more other cellular constituents in the collection. The cellular constituents making up a particular pathway can be drawn from any aspect of the biological state of a cell, for example, from the transcriptional state, or the translational state, or the activity state, or mixed aspects of the biological state. Therefore, cellular constituents of a pathway can include mRNA levels, protein abundances, protein activities, degree of protein or nucleic acid modification (e.g., phosphorylation or methylation), combinations of these types of cellular constituents, and so forth. Each cellular constituent of the collection is influenced by at least one other cellular constituent in the collection by some biological mechanism, which need not be specified or even known or understood. In illustrations presented herein, the influence, whether direct or indirect, of one cellular constituent on another is presented as an arc between the two cellular constituents, and the entire pathway is presented as a network of arcs linking the cellular constituents of the pathway. A biological pathway, therefore, refers both to the collection of cellular constituents drawn from some aspect of the biological state together with the network of influence between the constituents. Drugs and biological pathways are described in more detail in Marton and Stoughton, "Methods for Determining Therapeutic Index From Gene Expression Profiles," U.S. application Ser. No. 09/222,582 filed on even date herewith, incorporated herein by reference for all purposes.

5.2. Drug Concentration and Drug Response Profile

In some instances, it is preferred to choose a treatment dose in a model organism or a target subject in order to characterize drug interaction. When drug interaction is characterized in a target subject, the treatment dose may be an effective dose. Methods for determining an effective dose for a drug are well known in the art.

When drug interaction is characterized in a model organism, the treatment dose will typically be a concentration which (a) achieves an intracellular or receptor binding concentration roughly comparable to therapeutic concentrations of the drug in a target subject, and (b) produces a measurable set of responses in the constituent abundance levels, i.e. log(ratio) significantly different from zero for one or more constituents. In some preferred embodiments, a range of concentrations may be explored in a set of experiments to determine a good concentration for examining possible interactions.

FIG. 1 shows yeast *S. cerevisiae* mRNA response vs. concentration of the immunosuppressant drug FK506. Experimental methods were described in Marton et al., 1998, *Drug Target Validation And Identification of Secondary Drug Target Effects Using DNA Microarrays*, NATURE-MEDICINE 4:1293–301, incorporated herein by reference for all purposes. Dose response curves are plotted only for about 50 genes with the largest responses. In this case, it is found that a set of genes whose response is mediated by the primary (therapeutic) target of the drug (calcineurin) reach saturation response at lower concentrations (about 1 $\mu$g/ml) and a second set of genes responds at higher concentrations. In this case, any concentration near or above about 1 $\mu$g/ml would be informative, and the choice could be refined based on knowledge of the significance of the set of genes that responds at the higher concentrations.

In general it is not necessary to know the target of the drug—any concentration that yields a measurable signature is informative. However, one expects interaction effects to become more complex and severe at higher concentrations.

5.3. Predicting Overlay Response

A first type of drug interaction involves simple overlap of the responses of the two drugs with a resulting re-enforcement of their effects. Re-enforcement will occur in the overlap set of effects for any effects that are not completely saturated in the response of either drug alone. The term "overlap" as used herein does not necessarily imply linear superposition effect.

This re-enforcement or overlap effect may be dangerous in cases where the therapeutic concentrations are not too different from the toxic concentrations, i.e. in drugs or indications with a narrow therapeutic index. In some other cases, the re-enforcement effect may be beneficial.

One aspect of the invention provides methods to characterize such overlapping responses. In some embodiments, the responses of at least 2, preferably more than 5, more preferably more than 10 and most preferably more than 100 different cellular constituents to drugs A and B are measured. The relationship between response to drug A and response to drug B is analyzed by calculating the correlation coefficient between the two profiles. A high correlation coefficient or a set of cellular constituents in common indicates similarity of the responses and suggests that the simultaneous treatment with drug A and drug B will result in a larger response than that with either drug A or drug B alone.

In some other embodiments of the invention, the interaction effect of individual genes are analyzed by the similarity of the responses of individual genes to different drugs.

To verify the actual effects of overlap, which may not be a linear superposition of responses, or to detect nonlinear interactions, where new sets of effects result from simultaneous treatment that are not present in response to either individual treatment, experiments with simultaneous treatment with the two drugs are carried out.

Methods for calculating correlation coefficients are well within the skill of those in the art. For example, a brief description of correlations is available at www.statesoft.com ("Electronic Statistics Textbook," accessed on Dec. 22, 1998).

5.4. Nonlinear Interaction

The term 'nonlinear' as used herein refers to the effects of overlap that are not consistent with linear superposition, such as would occur in saturation of combined effects on a common pathway. Another typical nonlinear effect is the occurrence in the combined response of responses not seen in the response to individual drugs.

In one aspect of the invention, a biological sample is treated with drug A. The response of cellular constituents to drug A is monitored to obtain a first response profile. The biological sample is also treated with drug B first and then with drug A. The response of the biological sample in terms of cellular constituent changes to drug A (when drug B is present) is monitored to obtain a second profile. If the effects of drug A and B are additive, the second profile should be very similar to the first profile, i.e., it is not significantly affected by the presence or absence of drug B. If the interaction between drug A and drug B is nonlinear, the second profile will be different from the first response profile.

Figure 2:
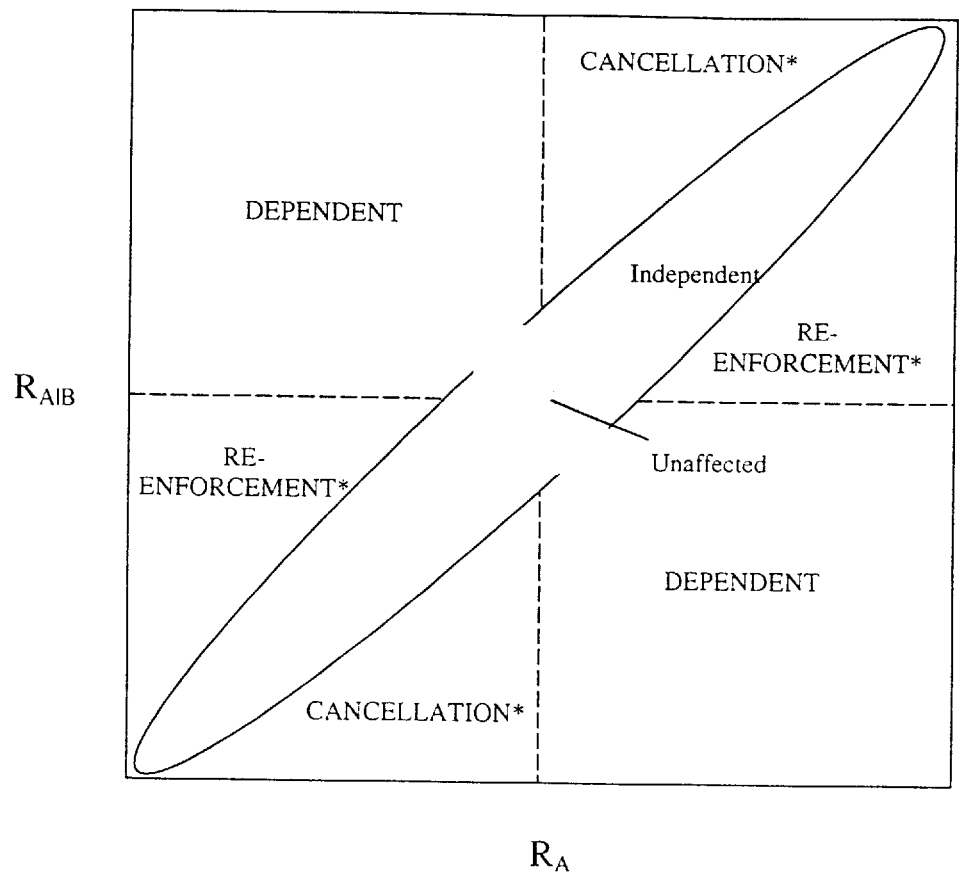
FIG. 2 shows graphic representation of interactions between drug A and drug B

In some embodiments of the invention, the interaction between drugs can be graphically examined. FIG. 2 illustrates some embodiments of this aspect of the invention. Each axis of FIG. 2 is the response of cellular constituents. Each cellular constituent is given two coordinates in this space according to its abundance ratio in the two condition pairs. The horizontal axis is response to drug A in the absence of other drugs (baseline), denoted $R_A$, while the vertical axis is the response to drug A in the presence of drug B, denoted $R_{A|B}$.

When error bars can be assigned to both coordinates of each cellular constituent plotted in FIG. 2, the membership in the different regions may be assigned with an objective statistical significance. In some instances, the error associated with each cellular constituents is derived from repeated measurements. In some other instances, the error associated with each measurement is derived from appropriate error models. Estimation of error associated with measurement, based upon error models, is well within the skill of one in the art. For example, in one particular embodiment, the response of each cellular constituent to drug A is repeatedly tested. The variation between tests is used to assign cellular constituents along the $R_A$ axis (horizontal axis) with statistical confidence. Similarly, the response of each cellular constituent to drug A in the presence of drug B is also repeatedly tested. The variation between the tests is used to assign cellular constituents along the $R_{A|B}$ axis (vertical axis). In some embodiments, the membership is assigned with 90% or greater statistical confidence, preferably with 95% or greater statistical confidence, and most preferably, 99% or greater statistical confidence. Cellular constituents in the central circle have small, measurement error dominated responses that are not significant. Cellular constituents in the long elliptical region along the 45° line have similar response whether or not B is present, and so are not candidates for interaction effects. Cellular constituents that fall in the upper left or lower right quadrants have responses to drug A that change sign depending on the presence of drug B. These are clearly drug B-dependent interaction effects, not associated with the overlap. Finally, a cellular constituent in the upper right or lower left quadrants but not in the elliptical region is a drug B-dependent interaction effect if it is not part of the overlap signature common to $\{R_A\}$ and $\{R_B\}$.

In some embodiments, the number of cellular constituents in different regions may be used as an indicator of overall interactions between drug A and drug B. When the methods of the invention are used to study the interaction between a number of drugs, the severity of interaction effect, in some instances, is ranked based upon the number of cellular constituents found to be significantly in upper left or lower right, or by number significantly away from the 45° line.

An overlap interaction may be explained as a re-enforcement or cancellation effect. In general, re-enforcement effects lead to partial saturation and a smaller effect in the A|B experiment (vertical axis) than in the A experiment (horizontal axis); cancellation (opposite competing effects of A and B on a given gene) leads to a potentially larger expression ratio in the A|B experiment since the abundance level can change from under-expression to over-expression, or from over-expression to under-expression.

The set of interaction effects may be interpreted biologically based on other knowledge of the function of the individual cellular constituents. Absent supporting biological information, the severity of the drug interaction is taken to be proportional to the number and magnitude of the interaction effects.

In some embodiments, drug B is administered with and without Drug A. This may give somewhat different interaction effects from administering drug A with and without Drug B. In some instances, both versions should be performed to be maximally informative. In other words, the $R_{A|B}$ vs. $R_A$ set of experiments and scatter plot, as above, and also the $R_{B|A}$ vs. $R_B$ set may be performed. Interaction effects that appear in both are of higher confidence than those that appear in either one alone, although these also may be real.

One of skill in the art would appreciate that the experimental procedure should be set up to minimize the effects of variations that are observed in the potency of drugs from experiment to repeated experiment. Even if these variations are not understood, the biases they introduce can be minimized in a model organism with, for example, the following procedure. To generate the $R_{A|B}$ and $R_A$ data, a culture may be treated first with A, then divided and one half is treated with B. Similarly, to generate the $R_{B|A}$ and $R_B$ data, a culture is first treated with B, then divided and one half of it is treated with A. This assures that the effects of the first drug treatment are identical in the two cultures.

However, this procedure is not equivalent to the $R_{A|B}$ vs. $R_A$ and $R_{B|A}$ vs. $R_B$ experiments described earlier. For example, when a culture is treated with drug A, then divided and one half is treated with drug B, the effects of drug A in the base line state and the effects of drug B in the A state are measured. The original definition of $R_{A|B}$ above was the effect of A in the B state. Both methods show drug interaction. The first method described above is more intuitively related to the concept of how the initial state of the cell influences response to a perturbation. The second method suffers less from the confusing effects of variation in effective drug potency from experiment to repeated experiment. One of skill would appreciate that a preferred method may be selected based upon the expected variation in effective drug potency.

It is preferable to have these experiments performed over a grid of concentration pairs of the two drug. In some preferred embodiments, however, four concentration pairs consisting of the four combinations of concentrations of the drugs (low and high end of the therapeutic range for each drug) are used.

A related alternative to the $R_{A|B}$ vs. $R_A$ method scatter plot described above is to compare the set of up and down regulations greater than a certain threshold in the individual vs. the joint drug treatment. Let $\{R_A\}$ be the set of significant (threshold crossing) response cellular constituents when treating with drug A, with similar definition for $\{R_B\}$ and let $\{R_{A,B}\}$ be the set of significant response genes when treating with both drugs. Interaction effects $\{I\}$ then can be defined according to $$\{R_{A,B}\} = \{R_A\} + \{R_B\} + \{I\} \tag{5}$$

This approach is less preferred than the $R_{A|B}$ vs. $R_A$ (and $R_{B|A}$ vs. $R_B$) method for the following reasons. First, whenever a set membership is defined by threshold, genes that are very close in their measurement values can be arbitrarily separated in their set assignments. Second, as mentioned above, it is observed that the effective concentration of a drug varies from experiment to repeated experiment. This means that, for example, if drug A is less potent for some reason in the A experiment than in the A, B experiment, many interaction effects that are really just due to enhanced potency of A in the combined-drug experiment may be falsely inferred. The $R_{A|B}$ vs. $R_A$ and $R_{A|B}$ vs. $R_A$ methods as described above control for this possible confusion and therefore is the preferred embodiment of the invention.

The methods of the invention are illustrated with the evaluation of interactions between a pair of drugs. However, these methods are also used to analyze the interaction among any number of drugs. In some embodiments, the interactions between two groups of drugs (group A and group B) are analyzed using the methods described above. In such embodiments, the response of cellular constituents to group A is monitored as $R_A$; the response of cellular constituents to group B is $R_B$; and the response of cellular constituents to group A in the presence of group B is $R_{A|B}$.

5.5. Model Organisms and Other Applications

The method of the invention is particularly useful for predicting drug interaction using a model organism. One preferred model organism for immunosuppressant drugs is yeast, *S. cerevisiae* in particular. Mammalian organisms or mammalian cell cultures may be used. In some embodiments, cells from the human patient to be treated can be cultured and used as a model to more reliably predict the drug interaction effects in that particular patient. Selecting appropriate model organisms for studying drug effects is well within the skill of those in the art.

The method of the invention is also applied to the analysis of multiple health risk (disease) factors. In such embodiments, each risk factor is associated with a response profile. The interaction between response profiles may be used to analyze the interactions between risk factors. For example, in one embodiment, response to risk factor A ($R_A$) and response to risk factor A in the presence of B ($R_{A|B}$) are plotted in FIG. 2 and analyzed as described for drugs A and B.

Response to risk factors is obtained, for example, by applying risk factors to a biological sample and measuring cellular constituent changes. In some other embodiments, cellular constituent profiles in response to risk factors may be obtained by surveys of individuals subject to such risk factors. In one particularly preferred embodiment, mRNAs of a large number of genes, preferably more than 100 genes, in the blood of a large number of individuals are measured. The risk factors those individuals have been exposed to are associated with the changes of mRNA levels in response to the level of the risk factors to obtain response profiles ($R_A$ and $R_{A|B}$, etc., where A and B are two different risk factors).

Evidence for profile components apparently arising from nonlinear interaction of individual risk factors would be indication of additional risk associated with the combined presence of the multiple risk factors above the sum of the individual risks.

5.6. Methods for Determining Biological Response Profiles

This invention utilizes the ability to measure the responses of a biological system to a large variety of perturbations. This section provides some exemplary methods for measuring biological responses. One of skill in the art would appreciate that this invention is not limited to the following specific methods for measuring the responses of a biological system.

5.6.1. Transcript Assay Using DNA Array

This invention is particularly useful for the analysis of gene expression profiles. One aspect of the invention provides methods for defining co-regulated genesets based upon the correlation of gene expression. Some embodiments of this invention are based on measuring the transcriptional rate of genes.

The transcriptional rate can be measured by techniques of hybridization to arrays of nucleic acid or nucleic acid mimic probes, described in the next subsection, or by other gene expression technologies, such as those described in the subsequent subsection. However measured, the result is either the absolute, relative amounts of transcripts or response data including values representing RNA abundance ratios, which usually reflect DNA expression ratios (in the absence of differences in RNA degradation rates).

In various alternative embodiments of the present invention, aspects of the biological state other than the transcriptional state, such as the translational state, the activity state, or mixed aspects can be measured.

Preferably, measurement of the transcriptional state is made by hybridization to transcript arrays, which are described in this subsection. Certain other methods of transcriptional state measurement are described later in this subsection.

In a preferred embodiment the present invention makes use of "transcript arrays" (also called herein "microarrays"). Transcript arrays can be employed for analyzing the transcriptional state in a biological sample and especially for measuring the transcriptional states of a biological sample exposed to graded levels of a drug of interest or to graded perturbations to a biological pathway of interest.

In one embodiment, transcript arrays are produced by hybridizing detectably labeled polynucleotides representing the mRNA transcripts present in a cell (e.g., fluorescently labeled cDNA synthesized from total cell mRNA) to a microarray. A microarray is a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain preferred characteristics: The arrays are reproducible, allowing multiple copies of a given array to be produced and easily compared with each other. Preferably the microarrays are small, usually smaller than 5 cm$^2$, and they are made from materials that are stable under binding (e.g., nucleic acid hybridization) conditions. A given binding site or unique set of binding sites in the microarray will specifically bind the product of a single gene in the cell. Although there may be more than one physical binding site (hereinafter "site") per specific mRNA, for the sake of clarity the discussion below will assume that there is a single site.

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cDNAs from two different cells are hybridized to the binding sites of the microarray. In the case of drug responses one biological sample is exposed to a drug and another biological sample of the same type is not exposed to the drug. In the case of pathway responses one cell is exposed to a pathway perturbation and another cell of the same type is not exposed to the pathway perturbation. The cDNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular mRNA detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the relative abundance of a particular mRNA in a cell, the mRNA will be equally prevalent in both cells and, upon reverse transcription, red-labeled and green-labeled cDNA will be equally prevalent. When hybridized to the microarray, the binding site(s) for that species of RNA will emit wavelengths characteristic of both fluorophores (and appear brown in combination). In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Shena et al., 1995, Quantitative monitoring of gene expression patterns with a complementary DNA microarray, Science 270:467–470, which is incorporated by reference in its entirety for all purposes. An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular mRNA in, e.g., a drug-treated or pathway-perturbed cell and an untreated cell.

5.6.1.1. Preparation of Microarrays

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often at least about 75%, more often at least about 85%, even more often more than about 90%, and most often at least about 99%. Preferably, the microarray has binding sites for genes relevant to the action of a drug of interest or in a biological pathway of interest. A "gene" is identified as an open reading frame (ORF) of preferably at least 50, 75, or 99 amino acids from which a messenger RNA is transcribed in the organism (e.g., if a single cell) or in some cell in a multicellular organism. The number of genes in a genome can be estimated from the number of mRNAs expressed by the organism, or by extrapolation from a well-characterized portion of the genome. When the genome of the organism of interest has been sequenced, the number of ORFs can be determined and mRNA coding regions identified by analysis of the DNA sequence. For example, the *Saccharomyces cerevisiae* genome has been completely sequenced and is reported to have approximately 6275 open reading frames (ORFs) longer than 99 amino acids. Analysis of these ORFs indicates that there are 5885 ORFs that are likely to specify protein products (Goffeau et al., 1996, Life with 6000 genes, Science 274:546–567, which is incorporated by reference in its entirety for all purposes). In contrast, the human genome is estimated to contain approximately $10^5$ genes.

5.6.1.2. Preparing Nucleic Acids for Microarrays

As noted above, the "binding site" to which a particular cognate cDNA specifically hybridizes is usually a nucleic acid or nucleic acid analogue attached at that binding site. In one embodiment, the binding sites of the microarray are DNA polynucleotides corresponding to at least a portion of each gene in an organism's genome. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, that result in amplification of unique fragments (i.e., fragments that do not share more than 10 bases of contiguous identical sequence with any other fragment on the microarray). Computer programs are useful in the design of primers with the required specificity and optimal amplification properties. See, e.g., Oligo version 5.0 (National Biosciences). In the case of binding sites corresponding to very long genes, it will sometimes be desirable to amplify segments near the 3' end of the gene so that when oligo-dT primed cDNA probes are hybridized to the microarray, less-than-full length probes will bind efficiently. Typically each gene fragment on the microarray will be between about 50 bp and about 2000 bp, more typically between about 100 bp and about 1000 bp, and usually between about 300 bp and about 800 bp in length. PCR methods are well known and are described, for example, in Innis et al. eds., 1990, PCR Protocols: A Guide to Methods and Applications, Academic Press Inc., San Diego, Calif., which is incorporated by reference in its entirety for all purposes. It will be apparent that computer controlled robotic systems are useful for isolating and amplifying nucleic acids.

An alternative means for generating the nucleic acid for the microarray is by synthesis of synthetic polynucleotides or oligonucleotides, e.g., using N-phosphonate or phosphoramidite chemistries (Froehler et al., 1986, Nucleic Acid Res 14:5399–5407; McBride et al., 1983, Tetrahedron Lett. 24:245–248). Synthetic sequences are between about 15 and about 500 bases in length, more typically between about 20 and about 50 bases. In some embodiments, synthetic nucleic acids include non-natural bases, e.g., inosine. As noted above, nucleic acid analogues may be used as binding sites for hybridization. An example of a suitable nucleic acid analogue is peptide nucleic acid (see, e.g., Egholm et al., 1993, PNA hybridizes to complementary oligonucleotides obeying the Watson-Crick hydrogen-bonding rules, Nature 365:566–568; see also U.S. Pat. No. 5,539,083).

In an alternative embodiment, the binding (hybridization) sites are made from plasmid or phage clones of genes, cDNAs (e.g., expressed sequence tags), or inserts therefrom (Nguyen et al., 1995, Differential gene expression in the murine thymus assayed by quantitative hybridization of arrayed cDNA clones, Genomics 29:207–209). In yet another embodiment, the polynucleotide of the binding sites is RNA.

5.6.1.3. Attaching Nucleic Acids to the Solid Surface

The nucleic acid or analogue are attached to a solid support, which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995, Quantitative monitoring of gene expression patterns with a complementary DNA microarray, Science 270:467–470. This method is especially useful for preparing microarrays of cDNA. See also DeRisi et al., 1996, Use of a cDNA microarray to analyze gene expression patterns in human cancer, Nature Genetics 14:457–460; Shalon et al., 1996, A DNA microarray system for analyzing complex DNA samples using two-color fluorescent probe hybridization, Genome Res. 6:639–645; and Schena et al., 1995, Parallel human genome analysis; microarray-based expression of 1000 genes, Proc. Natl. Acad. Sci. USA 93:10539–11286.

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Light-directed spatially addressable parallel chemical synthesis, Science 251:767–773; Pease et al., 1994, Light-directed oligonucleotide arrays for rapid DNA sequence analysis, Proc. Natl. Acad. Sci. USA 91:5022–5026; Lockhart et al., 1996, Expression monitoring by hybridization to high-density oligonucleotide arrays, Nature Biotech 14:1675; U.S. Pat. Nos. 5,578,832; 5,556,752; and 5,510,270, each of which is incorporated by reference in its entirety for all purposes) or other methods for rapid synthesis and deposition of defined oligonucleotides (Blanchard et al., 1996, High-Density Oligonucleotide arrays, Biosensors & Bioelectronics 11: 687–90). When these methods are used, oligonucleotides (e.g., 20-mers) of known sequence are synthesized directly on a surface such as a derivatized glass slide. Usually, the array produced contains multiple probes against each target transcript. Oligonucleotide probes can be chosen to detect alternatively spliced mRNAs or to serve as various type of control.

Another preferred method of making microarrays is by use of an inkjet printing process to synthesize oligonucleotides directly on a solid phase, as described, e.g., in co-pending U.S. patent application Ser. No. 09/008,120 filed on Jan. 16, 1998, by Blanchard entitled "Chemical Synthesis Using Solvent Microdroplets", which is incorporated by reference herein in its entirety.

Other methods for making microarrays, e.g., by masking (Maskos and Southern, 1992, Nuc. Acids Res. 20:1679–1684), may also be used. In principal, any type of array, for example, dot blots on a nylon hybridization membrane (see Sambrook et al., Molecular Cloning—A Laboratory Manual (2nd Ed.), Vol. 1–3, Cold Spring Harbor Laboratory, Cold Spring Harbor, N.Y., 1989), could be used, although, as will be recognized by those of skill in the art, very small arrays will be preferred because hybridization volumes will be smaller.

5.6.1.4. Generating Labeled Probes

Methods for preparing total and poly(A)+RNA are well known and are described generally in Sambrook et al., supra. In one embodiment, RNA is extracted from cells of the various types of interest in this invention using guanidinium thiocyanate lysis followed by CsCl centrifugation (Chirgwin et al., 1979, Biochemistry 18:5294–5299). Poly(A)+RNA is selected by selection with oligo-dT cellulose (see Sambrook et al., supra). Cells of interest include wild-type cells, drug-exposed wild-type cells, modified cells, and drug-exposed modified cells.

Labeled cDNA is prepared from mRNA by oligo dT-primed or random-primed reverse transcription, both of which are well known in the art (see, e.g., Klug and Berger, 1987, Methods Enzymol. 152:316–325). Reverse transcription may be carried out in the presence of a dNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, Expression monitoring by hybridization to high-density oligonucleotide arrays, Nature Biotech. 14:1675, which is incorporated by reference in its entirety for all purposes). In alternative embodiments, the cDNA or RNA probe can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent.

When fluorescently-labeled probes are used, many suitable fluorophores are known, including fluorescein, lissamine, phycoerythrin, rhodamine (Perkin Elmer Cetus), Cy2, Cy3, Cy3.5, Cy5, Cy5.5, Cy7, FluorX (Amersham) and others (see, e.g., Kricka, 1992, Nonisotopic DNA Probe Techniques, Academic Press San Diego, Calif.). It will be appreciated that pairs of fluorophores are chosen that have distinct emission spectra so that they can be easily distinguished.

In another embodiment, a label other than a fluorescent label is used. For example, a radioactive label, or a pair of radioactive labels with distinct emission spectra, can be used (see Zhao et al., 1995, High density cDNA filter analysis: a novel approach for large-scale, quantitative analysis of gene expression, Gene 156:207; Pietu et al., 1996, Novel gene transcripts preferentially expressed in human muscles revealed by quantitative hybridization of a high density cDNA array, Genome Res. 6:492). However, because of scattering of radioactive particles, and the consequent requirement for widely spaced binding sites, use of radioisotopes is a less-preferred embodiment.

In one embodiment, labeled cDNA is synthesized by incubating a mixture containing 0.5 mM dGTP, dATP and dCTP plus 0.1 mM dTTP plus fluorescent deoxyribonucleotides (e.g., 0.1 mM Rhodamine 110 UTP (Perken Elmer Cetus) or 0.1 mM Cy3 dUTP (Amersham)) with reverse transcriptase (e.g., SuperScript™ II, LTI Inc.) at 42° C. for 60 min.

5.6.1.5. Hybridization to Microarrays

Nucleic acid hybridization and wash conditions are optimally chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., supra).

Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., 1987, Current Protocols in Molecular Biology, Greene Publishing and Wiley-Interscience, New York. When the cDNA microarrays of Schena et al. are used, typical hybridization conditions are hybridization in 5×SSC plus 0.2% SDS at 65° C. for 4 hours followed by washes at 25° C. in low stringency wash buffer (1×SSC plus 0.2% SDS) followed by 10 minutes at 25° C. in high stringency wash buffer (0.1×SSC plus 0.2% SDS) (Shena et al., 1996, Proc. Natl. Acad. Sci. USA, 93:10614). Useful hybridization conditions are also provided in, e.g., Tijessen, 1993, Hybridization With Nucleic Acid Probes, Elsevier Science Publishers B.V. and Kricka, 1992, Nonisotopic DNA Probe Techniques, Academic Press San Diego, Calif.

5.6.1.6. Signal Detection and Data Analysis

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, A DNA microarray system for analyzing complex DNA samples using two-color fluorescent probe hybridization, Genome Research 6:639–645, which is incorporated by reference in its entirety for all purposes). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., 1996, Genome Res. 6:639–645 and in other references cited herein. Alternatively, the fiber-optic bundle described by Ferguson et al., 1996, Nature Biotech. 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA in two biological samples is scored as a perturbation and its magnitude determined (i.e., the abundance is different in the two sources of mRNA tested), or as not perturbed (i.e., the relative abundance is the same). In various embodiments, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

5.6.2. Pathway Response and Genesets

In one embodiment of the present invention, genesets are determined by observing the gene expression response of perturbation to a particular pathway. In one embodiment of the invention, transcript arrays reflecting the transcriptional state of a biological sample of interest are made by hybridizing a mixture of two differently labeled probes each corresponding (i.e., complementary) to the mRNA of a different sample of interest, to the microarray. According to the present invention, the two samples are of the same type, i.e., of the same species and strain, but may differ genetically at a small number (e.g., one, two, three, or five, preferably one) of loci. Alternatively, they are isogeneic and differ in their environmental history (e.g., exposed to a drug versus not exposed). The genes whose expression are highly correlated may belong to a geneset.

In one aspect of the invention, gene expression change in response to a large number of perturbations is used to construct a clustering tree for the purpose of defining genesets. Preferably, the perturbations should target different pathways. In order to measure expression responses to the pathway perturbation, biological samples are subjected to graded perturbations to pathways of interest. The samples exposed to the perturbation and samples not exposed to the perturbation are used to construct transcript arrays, which are measured to find the mRNAs with modified expression and the degree of modification due to exposure to the perturbation. Thereby, the perturbation-response relationship is obtained.

The density of levels of the graded drug exposure and graded perturbation control parameter is governed by the sharpness and structure in the individual gene responses—the steeper the steepest part of the response, the denser the levels needed to properly resolve the response.

Further, it is preferable in order to reduce experimental error to reverse the fluorescent labels in two-color differential hybridization experiments to reduce biases peculiar to individual genes or array spot locations. In other words, it is preferable to first measure gene expression with one labeling (e.g., labeling perturbed cells with a first fluorochrome and unperturbed cells with a second fluorochrome) of the mRNA from the two cells being measured, and then to measure gene expression from the two cells with reversed labeling (e.g., labeling perturbed cells with the second fluorochrome and unperturbed cells with the first fluorochrome). Multiple measurements over exposure levels and perturbation control parameter levels provide additional experimental error control. With adequate sampling a trade-off may be made when choosing the width of the spline function S used to interpolate response data between averaging of errors and loss of structure in the response functions.

5.6.3. Measurement of Graded Perturbation Response Data

To measure graded response data, the cells are exposed to graded levels of the drug, drug candidate of interest or grade strength of other perturbation. When the cells are grown in vitro, the compound is usually added to their nutrient medium. In the case of yeast, it is preferable to harvest the yeast in early log phase, since expression patterns are relatively insensitive to time of harvest at that time. Several levels of the drug or other compounds are added. The particular level employed depends on the particular characteristics of the drug, but usually will be between about 1 ng/ml and 100 mg/ml. In some cases a drug will be solubilized in a solvent such as DMSO.

The cells exposed to the drug and cells not exposed to the drug are used to construct transcript arrays, which are measured to find the mRNAs with altered expression due to exposure to the drug. Thereby, the drug response is obtained.

Similarly for measurements of pathway responses, it is preferable also for drug responses, in the case of two-color differential hybridization, to measure also with reversed labeling. Also, it is preferable that the levels of drug exposure used proved sufficient resolution (e.g., by using approximately 10 levels of drug exposure) of rapidly changing regions of the drug response.

5.6.4. Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, Proc. Natl. Acad. Sci. USA 93:659–663). Other methods statistically sample cDNA pools, such as by sequencing sufficient bases (e.g., 20–50 bases) in each of multiple cDNAs to identify each cDNA, or by sequencing short tags (e.g., 9–10 bases) which are generated at known positions relative to a defined mRNA end (see, e.g., Velculescu, 1995, Science 270:484–487).

5.6.5. Measurement of Other Aspects of Biological State

In various embodiments of the present invention, aspects of the biological state other than the transcriptional state, such as the translational state, the activity state, or mixed aspects can be measured in order to obtain drug and pathway responses. Details of these embodiments are described in this section.

5.6.5.1. Embodiments Based on Translational State Measurements

Measurement of the translational state may be performed according to several methods. For example, whole genome monitoring of protein (i.e., the "proteome," Goffeau et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, Antibodies: A Laboratory Manual, Cold Spring Harbor, N.Y., which is incorporated in its entirety for all purposes). In a preferred embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, Gel Electrophoresis of Proteins: A Practical Approach, IRL Press, New York; Shevchenko et al., 1996, Proc. Nat'l Acad. Sci. USA 93:1440–1445; Sagliocco et al., 1996, Yeast 12:1519–1533; Lander, 1996, Science 274:536–539. The resulting electropherograms can be analyzed by numerous techniques, including mass spectrometric techniques, western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or overexpression of a specific gene.

5.6.5.2. Embodiments Based on Other Aspects of the Biological State

Even though methods of this invention are illustrated by embodiments involving gene expression profiles, the methods of the invention are applicable to any cellular constituent that can be monitored.

In particular, where activities of proteins relevant to the characterization of a perturbation, such as drug action, can be measured, embodiments of this invention can be based on such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In alternative and non-limiting embodiments, response data may be formed of mixed aspects of the biological state of a cell. Response data can be constructed from, e.g., changes in certain mRNA abundances, changes in certain protein abundances, and changes in certain protein activities.

5.7. Method for Probing Cellular States

One aspect of the invention provides methods for the analysis of co-varying cellular constituents. The methods of this invention are also useful for the analysis of responses of a biological sample to perturbations designed to probe cellular state. This section provides some illustrative methods for probing cellular states.

Methods for targeted perturbation of cellular states at various levels of a cell are increasingly widely known and applied in the art. Any such methods that are capable of specifically targeting and controllably modifying (e.g., either by a graded increase or activation or by a graded decrease or inhibition) specific cellular constituents (e.g., gene expression, RNA concentrations, protein abundances, protein activities, or so forth) can be employed in performing cellular state perturbations. Controllable modifications of cellular constituents consequentially controllably perturb cellular states originating at the modified cellular constituents. Preferable modification methods are capable of individually targeting each of a plurality of cellular constituents and most preferably a substantial fraction of such cellular constituents.

The following methods are exemplary of those that can be used to modify cellular constituents and thereby to produce cellular state perturbations which generate the cellular state responses used in the steps of the methods of this invention as previously described. This invention is adaptable to other methods for making controllable perturbations to cellular states, and especially to cellular constituents from which cellular states originate.

Cellular state perturbations are preferably made in cells of cell types derived from any organism for which genomic or expressed sequence information is available and for which methods are available that permit controllable modification of the expression of specific genes. Genome sequencing is currently underway for several eukaryotic organisms, including humans, nematodes, Arabidopsis, and flies. In a preferred embodiment, the invention is carried out using a yeast, with *Saccharomyces cerevisiae* most preferred because the sequence of the entire genome of a *S. cerevisiae* strain has been determined. In addition, well-established methods are available for controllably modifying expression of yeast genes. A preferred strain of yeast is a *S. cerevisiae* strain for which yeast genomic sequence is known, such as strain S288C or substantially isogeneic derivatives of it (see, e.g., Nature 369, 371–8 (1994); *P.N.A.S.* 92:3809–13 (1995); *E.M.B.O.J.* 13:5795–5809 (1994), Science 265:2077–2082 (1994); *E.M.B.O.J.* 15:2031–49 (1996), all of which are incorporated herein. However, other strains may be used as well. Yeast strains are available from American Type Culture Collection, Manassas, Va. Standard techniques for manipulating yeast are described in C. Kaiser, S. Michaelis, & A. Mitchell, 1994, Methods in Yeast Genetics: A Cold Spring Harbor Laboratory Course Manual, Cold Spring Harbor Laboratory Press, New York; and Sherman et al., 1986, Methods in Yeast Genetics: A Laboratory Manual, Cold Spring Harbor Laboratory, Cold Spring Harbor. N.Y., both of which are incorporated by reference in their entirety and for all purposes.

The exemplary methods described in the following include use of titratable expression systems, use of transfection or viral transduction systems, direct modifications to RNA abundances or activities, direct modifications of protein abundances, and direct modification of protein activities including use of drugs (or chemical moieties in general) with specific known action.

5.7.1. Titratable Expression Systems

Any of the several known titratable, or equivalently controllable, expression systems available for use in the budding yeast *Saccharomyces cerevisiae* are adaptable to this invention (Mumberg et al., 1994, Regulatable promoter of *Saccharomyces cerevisiae:* comparison of transcriptional activity and their use for heterologous expression, Nucl. Acids Res. 22:5767–5768). Usually, gene expression is controlled by transcriptional controls, with the promoter of the gene to be controlled replaced on its chromosome by a controllable, exogenous promoter. The most commonly used controllable promoter in yeast is the GAL1 promoter (Johnston et al., 1984, Sequences that regulate the divergent GAL1–GAL10 promoter in *Saccharomyces cerevisiae,* Mol Cell. Biol. 8:1440–1448). The GAL1 promoter is strongly repressed by the presence of glucose in the growth medium, and is gradually switched on in a graded manner to high levels of expression by the decreasing abundance of glucose and the presence of galactose. The GAL1 promoter usually allows a 5–100 fold range of expression control on a gene of interest.

Other frequently used promoter systems include the MET25 promoter (Kerjan et al., 1986, Nucleotide sequence of the *Saccharomyces cerevisiae* MET25 gene, Nucl. Acids. Res. 14:7861–7871), which is induced by the absence of methionine in the growth medium, and the CUP1 promoter, which is induced by copper (Mascorro-Gallardo et al., 1996, Construction of a CUP1 promoter-based vector to modulate gene expression in *Saccharomyces cerevisiae,* Gene 172:169–170). All of these promoter systems are controllable in that gene expression can be incrementally controlled by incremental changes in the abundances of a controlling moiety in the growth medium.

One disadvantage of the above listed expression systems is that control of promoter activity (effected by, e.g., changes in carbon source, removal of certain amino acids), often causes other changes in cellular physiology which independently alter the expression levels of other genes. A recently developed system for yeast, the Tet system, alleviates this problem to a large extent (Gari et al., 1997, A set of vectors with a tetracycline-regulatable promoter system for modulated gene expression in *Saccharomyces cerevisiae,* Yeast 13:837–848). The Tet promoter, adopted from mammalian expression systems (Gossen et al., 1995, Transcriptional activation by tetracyclines in mammalian cells, Proc. Nat. Acad. Sci. USA 89:5547–5551) is modulated by the concentration of the antibiotic tetracycline or the structurally related compound doxycycline. Thus, in the absence of doxycycline, the promoter induces a high level of expression, and the addition of increasing levels of doxycycline causes increased repression of promoter activity. Intermediate levels of gene expression can be achieved in the steady state by addition of intermediate levels of drug. Furthermore, levels of doxycycline that give maximal repression of promoter activity (10 micrograms/ml) have no significant effect on the growth rate on wild type yeast cells (Gari et al., 1997, A set of vectors with a tetracycline-regulatable promoter system for modulated gene expression in *Saccharomyces cerevisiae,* Yeast 13:837–848).

In mammalian cells, several means of titrating expression of genes are available (Spencer, 1996, Creating conditional mutations in mammals, Trends Genet. 12:181–187). As mentioned above, the Tet system is widely used, both in its original form, the "forward" system, in which addition of doxycycline represses transcription, and in the newer "reverse" system, in which doxycycline addition stimulates transcription (Gossen et al., 1995, Proc. Natl. Acad. Sci. USA 89:5547–5551; Hoffmann et al., 1997, Nucl. Acids. Res. 25:1078–1079; Hoffmann et al., 1996, Proc. Natl. Acad. Sci. USA 83:5185–5190; Paulus et al., 1996, Journal of Virology 70:62–67). Another commonly used controllable promoter system in mammalian cells is the ecdysone-inducible system developed by Evans and colleagues (No et al., 1996, Ecdysone-inducible gene expression in mammalian cella and transgenic mice, Proc. Nat. Acad. Sci. USA 93:3346–3351), where expression is controlled by the level of muristerone added to the cultured cells. Finally, expression can be modulated using the "chemical-induced dimerization" (CID) system developed by Schreiber, Crabtree, and colleagues (Belshaw et al., 1996, Controlling protein association and subcellular localization with a synthetic ligand that induces heterodimerization of proteins, Proc. Nat. Acad. Sci. USA 93:4604–4607; Spencer, 1996, Creating conditional mutations in mammals, Trends Genet. 12:181–187) and similar systems in yeast. In this system, the gene of interest is put under the control of the CID-responsive promoter, and transfected into cells expressing two different hybrid proteins, one comprised of a DNA-binding domain fused to FKBP12, which binds FK506. The other hybrid protein contains a transcriptional activation domain also fused to FKBP12. The CID inducing molecule is FK1012, a homodimeric version of FK506 that is able to bind simultaneously both the DNA binding and transcriptional activating hybrid proteins. In the graded presence of FK1012, graded transcription of the controlled gene is activated.

For each of the mammalian expression systems described above, as is widely known to those of skill in the art, the gene of interest is put under the control of the controllable promoter, and a plasmid harboring this construct along with an antibiotic resistance gene is transfected into cultured mammalian cells. In general, the plasmid DNA integrates into the genome, and drug resistant colonies are selected and screened for appropriate expression of the regulated gene. Alternatively, the regulated gene can be inserted into an episomal plasmid such as pCEP4 (Invitrogen, Inc.), which contains components of the Epstein-Barr virus necessary for plasmid replication.

In a preferred embodiment, titratable expression systems, such as the ones described above, are introduced for use into cells or organisms lacking the corresponding endogenous gene and/or gene activity, e.g., organisms in which the endogenous gene has been disrupted or deleted. Methods for producing such "knock outs" are well known to those of skill in the art, see e.g., Pettitt et al., 1996, Development 122:4149–4157; Spradling et al., 1995, Proc. Natl. Acad. Sci. USA, 92:10824–10830; Ramirez-Solis et al., 1993, Methods Enzymol. 225:855–878; and Thomas et al., 1987, Cell 51:503–512.

5.7.2. Transfection Systems for Mammalian Cells

Transfection or viral transduction of target genes can introduce controllable perturbations in biological cellular states in mammalian cells. Preferably, transfection or transduction of a target gene can be used with cells that do not naturally express the target gene of interest. Such non-expressing cells can be derived from a tissue not normally expressing the target gene or the target gene can be specifically mutated in the cell. The target gene of interest can be cloned into one of many mammalian expression plasmids, for example, the pcDNA3.1 +/– system (Invitrogen, Inc.) or retroviral vectors, and introduced into the non-expressing host cells. Transfected or transduced cells expressing the target gene may be isolated by selection for a drug resistance marker encoded by the expression vector. The level of gene transcription is monotonically related to the transfection dosage. In this way, the effects of varying levels of the target gene may be investigated.

A particular example of the use of this method is the search for drugs that target the src-family protein tyrosine kinase, lck, a key component of the T cell receptor activation cellular state (Anderson et al., 1994, Involvement of the protein tyrosine kinase p56 (lck) in T cell signaling and thymocyte development, Adv. Immunol. 56:171–178). Inhibitors of this enzyme are of interest as potential immunosuppressive drugs (Hanke, 1996, Discovery of a Novel, Potent, and src family-selective tyrosine kinase inhibitor, J. Biol Chem 271:695–701). A specific mutant of the Jurkat T cell line (JcaM1) is available that does not express Ick kinase (Straus et al., 1992, Genetic evidence for the involvement of the lck tyrosine kinase in signal transduction through the T cell antigen receptor, Cell 70:585–593). Therefore, introduction of the Ick gene into JCaM1 by transfection or transduction permits specific perturbation of cellular states of T cell activation regulated by the lck kinase. The efficiency of transfection or transduction, and thus the level of perturbation, is dose related. The method is generally useful for providing perturbations of gene expression or protein abundances in cells not normally expressing the genes to be perturbed.

5.7.3. Methods of Modifying RNA Abundances or Activities

Methods of modifying RNA abundances and activities currently fall within three classes, ribozymes, antisense species, and RNA aptamers (Good et al., 1997, Gene Therapy 4: 45–54). Controllable application or exposure of a cell to these entities permits controllable perturbation of RNA abundances.

Ribozymes are RNAs which are capable of catalyzing RNA cleavage reactions. (Cech, 1987, Science 236:1532–1539; PCT International Publication WO 90/11364, published Oct. 4, 1990; Sarver et al., 1990, Science 247: 1222–1225). "Hairpin" and "hammerhead" RNA ribozymes can be designed to specifically cleave a particular target mRNA. Rules have been established for the design of short RNA molecules with ribozyme activity, which are capable of cleaving other RNA molecules in a highly sequence specific way and can be targeted to virtually all kinds of RNA. (Haseloff et al., 1988, Nature 334:585–591; Koizumi et al., 1988, FEBS Lett., 228:228–230; Koizumi et al., 1988, FEBS Lett., 239:285–288). Ribozyme methods involve exposing a cell to, inducing expression in a cell, etc. of such small RNA ribozyme molecules. (Grassi and Marini, 1996, Annals of Medicine 28: 499–510; Gibson, 1996, Cancer and Metastasis Reviews 15: 287–299).

Ribozymes can be routinely expressed in vivo in sufficient number to be catalytically effective in cleaving mRNA, and thereby modifying mRNA abundances in a cell. (Cotten et al., 1989, Ribozyme mediated destruction of RNA in vivo, The EMBO J. 8:3861–3866). In particular, a ribozyme coding DNA sequence, designed according to the previous rules and synthesized, for example, by standard phosphoramidite chemistry, can be ligated into a restriction enzyme site in the anticodon stem and loop of a gene encoding a tRNA, which can then be transformed into and expressed in a cell of interest by methods routine in the art. Preferably, an inducible promoter (e.g., a glucocorticoid or a tetracycline response element) is also introduced into this construct so that ribozyme expression can be selectively controlled. tDNA genes (i.e., genes encoding tRNAs) are useful in this application because of their small size, high rate of transcription, and ubiquitous expression in different kinds of tissues. Therefore, ribozymes can be routinely designed to cleave virtually any mRNA sequence, and a cell can be routinely transformed with DNA coding for such ribozyme sequences such that a controllable and catalytically effective amount of the ribozyme is expressed. Accordingly the abundance of virtually any RNA species in a cell can be perturbed.

In another embodiment, activity of a target RNA (preferable mRNA) species, specifically its rate of translation, can be controllably inhibited by the controllable application of antisense nucleic acids. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered in a controllable manner to a cell or which can be produced intracellularly by transcription of exogenous, introduced sequences in controllable quantities sufficient to perturb translation of the target RNA.

Preferably, antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86: 6553–6556; Lemaitre et al., 1987, Proc. Natl. Acad. Sci. 84: 648–652; PCT Publication No. WO 88/09810, published Dec. 15, 1988), hybridization-triggered cleavage agents (see, e.g., Krol et al., 1988, BioTechniques 6: 958–976) or intercalating agents (see, e.g., Zon, 1988, Pharm. Res. 5: 539–549).

In a preferred aspect of the invention, an antisense oligonucleotide is provided, preferably as single-stranded DNA. The oligonucleotide may be modified at any position on its structure with constituents generally known in the art.

The antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is a 2-α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15: 6625–6641).

The oligonucleotide may be conjugated to another molecule, e.g., a peptide, hybridization triggered cross-linking agent, transport agent, hybridization-triggered cleavage agent, etc.

The antisense nucleic acids of the invention comprise a sequence complementary to at least a portion of a target RNA species. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a target RNA it may contain and still form a stable duplex (or triplex, as the case may be). One skilled in the art can ascertain a tolerable degree of mismatch by use of standard procedures to determine the melting point of the hybridized complex. The amount of antisense nucleic acid that will be effective in the inhibiting translation of the target RNA can be determined by standard assay techniques.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16: 3209), methylphosphonate oligonucleotides can be prepared by use of controlled pore glass polymer supports (Sarin et al., 1988, Proc. Natl. Acad. Sci. U.S.A. 85: 7448–7451), etc. In another embodiment, the oligonucleotide is a 2'-0-methylribonucleotide (Inoue et al., 1987, Nucl. Acids Res. 15: 6131–6148), or a chimeric RNA-DNA analog (Inoue et al., 1987, FEBS Lett. 215: 327–330).

The synthesized antisense oligonucleotides can then be administered to a cell in a controlled manner. For example, the antisense oligonucleotides can be placed in the growth environment of the cell at controlled levels where they may be taken up by the cell. The uptake of the antisense oligonucleotides can be assisted by use of methods well known in the art.

In an alternative embodiment, the antisense nucleic acids of the invention are controllably expressed intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the antisense RNAs can be by any promoter known in the art to act in a cell of interest. Such promoters can be inducible or constitutive. Most preferably, promoters are controllable or inducible by the administration of an exogenous moiety in order to achieve controlled expression of the antisense oligonucleotide. Such controllable promoters include the Tet promoter. Less preferably usable promoters for mammalian cells include, but are not limited to: the SV40 early promoter region (Bernoist and Chambon, 1981, Nature 290: 304–310), the promoter contained in the 3' long terminal repeat of Rous sarcoma virus (Yamamoto et al., 1980, Cell 22: 787–797), the herpes thymidine kinase promoter (Wagner et al., 1981, Proc. Natl. Acad. Sci. U.S.A. 78: 1441–1445), the regulatory sequences of the metallothionein gene (Brinster et al., 1982, Nature 296: 39–42), etc.

Therefore, antisense nucleic acids can be routinely designed to target virtually any mRNA sequence, and a cell can be routinely transformed with or exposed to nucleic acids coding for such antisense sequences such that an effective and controllable amount of the antisense nucleic acid is expressed. Accordingly the translation of virtually any RNA species in a cell can be controllably perturbed.

Finally, in a further embodiment, RNA aptamers can be introduced into or expressed in a cell. RNA aptamers are specific RNA ligands for proteins, such as for Tat and Rev RNA (Good et al., 1997, Gene Therapy 4: 45–54) that can specifically inhibit their translation.

5.7.4. Methods of Modifying Protein Abundances

Methods of modifying protein abundances include, inter alia, those altering protein degradation rates and those using antibodies (which bind to proteins affecting abundances of activities of native target protein species). Increasing (or decreasing) the degradation rates of a protein species decreases (or increases) the abundance of that species. Methods for controllably increasing the degradation rate of a target protein in response to elevated temperature and/or exposure to a particular drug, which are known in the art, can be employed in this invention. For example, one such method employs a heat-inducible or drug-inducible N-terminal degron, which is an N-terminal protein fragment that exposes a degradation signal promoting rapid protein degradation at a higher temperature (e.g., 37° C.) and which is hidden to prevent rapid degradation at a lower temperature (e.g., 23° C.) (Dohmen et. al, 1994, Science 263:1273–1276). Such an exemplary degron is Arg-DHFR$^{ts}$, a variant of murine dihydrofolate reductase in which the N-terminal Val is replaced by Arg and the Pro at position 66 is replaced with Leu. According to this method, for example, a gene for a target protein, P, is replaced by standard gene targeting methods known in the art (Lodish et al., 1995, *Molecular Biology of the Cell,* W. H. Freeman and Co., New York, especially chap 8) with a gene coding for the fusion protein Ub-Arg-DHFR$^{ts}$-P ("Ub" stands for ubiquitin). The N-terminal ubiquitin is rapidly cleaved after translation exposing the N-terminal degron. At lower temperatures, lysines internal to Arg-DHFR$^{ts}$ are not exposed, ubiquitination of the fusion protein does not occur, degradation is slow, and active target protein levels are high. At higher temperatures (in the absence of methotrexate), lysines internal to Arg-DHFR$^{ts}$ are exposed, ubiquitination of the fusion protein occurs, degradation is rapid, and active target protein levels are low. Heat activation of degradation is controllably blocked by exposure methotrexate. This method is adaptable to other N-terminal degrees which are responsive to other inducing factors, such as drugs and temperature changes.

Target protein abundances and also, directly or indirectly, their activities can also be decreased by (neutralizing) antibodies. By providing for controlled exposure to such antibodies, protein abundances/activities can be controllably modified. For example, antibodies to suitable epitopes on protein surfaces may decrease the abundance, and thereby indirectly decrease the activity, of the wild-type active form of a target protein by aggregating active forms into complexes with less or minimal activity as compared to the wild-type unaggregated wild-type form. Alternately, antibodies may directly decrease protein activity by, e.g., interacting directly with active sites or by blocking access of substrates to active sites. Conversely, in certain cases, (activating) antibodies may also interact with proteins and their active sites to increase resulting activity. In either case, antibodies (of the various types to be described) can be raised against specific protein species (by the methods to be described) and their effects screened. The effects of the antibodies can be assayed and suitable antibodies selected that raise or lower the target protein species concentration and/or activity. Such assays involve introducing antibodies into a cell (see below), and assaying the concentration of the wild-type amount or activities of the target protein by standard means (such as immunoassays) known in the art. The net activity of the wild-type form can be assayed by assay means appropriate to the known activity of the target protein.

Antibodies can be introduced into cells in numerous fashions, including, for example, microinjection of antibodies into a cell (Morgan et al., 1988, Immunology Today 9:84–86) or transforming hybridoma mRNA encoding a desired antibody into a cell (Burke et al., 1984, Cell 36:847–858). In a further technique, recombinant antibodies can be engineering and ectopically expressed in a wide variety of non-lymphoid cell types to bind to target proteins as well as to block target protein activities (Biocca et al, 1995, Trends in Cell Biology 5:248–252). Preferably, expression of the antibody is under control of a controllable promoter, such as the Tet promoter. A first step is the selection of a particular monoclonal antibody with appropriate specificity to the target protein (see below). Then sequences encoding the variable regions of the selected antibody can be cloned into various engineered antibody formats, including, for example, whole antibody, Fab fragments, Fv fragments, single chain Fv fragments ($V_H$ and $V_L$ regions united by a peptide linker) ("ScFv" fragments), diabodies (two associated ScFv fragments with different specificities), and so forth (Hayden et al., 1997, Current Opinion in Immunology 9:210–212). Intracellularly expressed antibodies of the various formats can be targeted into cellular compartments (e.g., the cytoplasm, the nucleus, the mitochondria, etc.) by expressing them as fusions with the various known intracellular leader sequences (Bradbury et al., 1995, Antibody Engineering (vol. 2) (Borrebaeck ed.), pp 295–361, IRL Press). In particular, the ScFv format appears to be particularly suitable for cytoplasmic targeting.

Antibody types include, but are not limited to, polyclonal, monoclonal, chimeric, single chain, Fab fragments, and an Fab expression library. Various procedures known in the art may be used for the production of polyclonal antibodies to a target protein. For production of the antibody, various host animals can be immunized by injection with the target protein, such host animals include, but are not limited to, rabbits, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacillus Calmette-Guerin (BCG) and corynebacterium parvum.

For preparation of monoclonal antibodies directed towards a target protein, any technique that provides for the production of antibody molecules by continuous cell lines in culture may be used. Such techniques include, but are not restricted to, the hybridoma technique originally developed by Kohler and Milstein (1975, Nature 256: 495–497), the trioma technique, the human B-cell hybridoma technique (Kozbor et al., 1983, Immunology Today 4: 72), and the EBV hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. USA 80: 2026–2030), or by transforming human B cells with EBV virus in vitro (Cole et al., 1985, in Monoclonal Antibodies and Cancer Therapy, Alan R. Liss, Inc., pp. 77–96). In fact, according to the invention, techniques developed for the production of "chimeric antibodies" (Morrison et al., 1984, Proc. Natl. Acad. Sci. USA 81: 6851–6855; Neuberger et al., 1984, Nature 312:604–608; Takeda et al., 1985, Nature 314: 452–454) by splicing the genes from a mouse antibody molecule specific for the target protein together with genes from a human antibody molecule of appropriate biological activity can be used; such antibodies are within the scope of this invention.

Additionally, where monoclonal antibodies are advantageous, they can be alternatively selected from large antibody libraries using the techniques of phage display (Marks et al., 1992, J. Biol. Chem. 267:16007–16010). Using this technique, libraries of up to $10^{12}$ different antibodies have been expressed on the surface of fd filamentous phage, creating a "single pot" in vitro immune system of antibodies available for the selection of monoclonal antibodies (Griffiths et al., 1994, EMBO J. 13:3245–3260). Selection of antibodies from such libraries can be done by techniques known in the art, including contacting the phage to immobilized target protein, selecting and cloning phage bound to the target, and subcloning the sequences encoding the antibody variable regions into an appropriate vector expressing a desired antibody format.

According to the invention, techniques described for the production of single chain antibodies (U.S. Pat. No. 4,946, 778) can be adapted to produce single chain antibodies specific to the target protein. An additional embodiment of the invention utilizes the techniques described for the construction of Fab expression libraries (Huse et al., 1989, Science 246: 1275–1281) to allow rapid and easy identification of monoclonal Fab fragments with the desired specificity for the target protein.

Antibody fragments that contain the idiotypes of the target protein can be generated by techniques known in the art. For example, such fragments include, but are not limited to: the F(ab')₂ fragment which can be produced by pepsin digestion of the antibody molecule; the Fab' fragments that can be generated by reducing the disulfide bridges of the F(ab')₂ fragment, the Fab fragments that can be generated by treating the antibody molecule with papain and a reducing agent, and Fv fragments.

In the production of antibodies, screening for the desired antibody can be accomplished by techniques known in the art, e.g., ELISA (enzyme-linked immunosorbent assay). To select antibodies specific to a target protein, one may assay generated hybridomas or a phage display antibody library for an antibody that binds to the target protein.

5.7.5. Methods of Modifying Protein Activities

Methods of directly modifying protein activities include, inter alia, dominant negative mutations, specific drugs (used in the sense of this application) or chemical moieties generally, and also the use of antibodies, as previously discussed.

Dominant negative mutations are mutations to endogenous genes or mutant exogenous genes that when expressed in a cell disrupt the activity of a targeted protein species. Depending on the structure and activity of the targeted protein, general rules exist that guide the selection of an appropriate strategy for constructing dominant negative mutations that disrupt activity of that target (Hershkowitz, 1987, Nature 329:219–222). In the case of active monomeric forms, over expression of an inactive form can cause competition for natural substrates or ligands sufficient to significantly reduce net activity of the target protein. Such over expression can be achieved by, for example, associating a promoter, preferably a controllable or inducible promoter, of increased activity with the mutant gene. Alternatively, changes to active site residues can be made so that a virtually irreversible association occurs with the target ligand. Such can be achieved with certain tyrosine kinases by careful replacement of active site serine residues (Perlmutter et al., 1996, Current Opinion in Immunology 8:285–290).

In the case of active multimeric forms, several strategies can guide selection of a dominant negative mutant. Multimeric activity can be controllably decreased by expression of genes coding exogenous protein fragments that bind to multimeric association domains and prevent multimer formation. Alternatively, controllable over expression of an inactive protein unit of a particular type can tie up wild-type active units in inactive multimers, and thereby decrease multimeric activity (Nocka et al., 1990, The EMBO J. 9:1805–1813). For example, in the case of dimeric DNA binding proteins, the DNA binding domain can be deleted from the DNA binding unit, or the activation domain deleted from the activation unit. Also, in this case, the DNA binding domain unit can be expressed without the domain causing association with the activation unit. Thereby, DNA binding sites are tied up without any possible activation of expression. In the case where a particular type of unit normally undergoes a conformational change during activity, expression of a rigid unit can inactivate resultant complexes. For a further example, proteins involved in cellular mechanisms, such as cellular motility, the mitotic process, cellular architecture, and so forth, are typically composed of associations of many subunits of a few types. These structures are often highly sensitive to disruption by inclusion of a few monomeric units with structural defects. Such mutant monomers disrupt the relevant protein activities and can be controllably expressed in a cell.

In addition to dominant negative mutations, mutant target proteins that are sensitive to temperature (or other exogenous factors) can be found by mutagenesis and screening procedures that are well-known in the art.

Also, one of skill in the art will appreciate that expression of antibodies binding and inhibiting a target protein can be employed as another dominant negative strategy.

Finally, activities of certain target proteins can be controllably altered by exposure to exogenous drugs or ligands. In a preferable case, a drug is known that interacts with only one target protein in the cell and alters the activity of only that one target protein. Graded exposure of a cell to varying amounts of that drug thereby causes graded perturbations of cellular states originating at that protein. The alteration can be either a decrease or an increase of activity. Less preferably, a drug is known and used that alters the activity of only a few (e.g., 2–5) target proteins with separate, distinguishable, and non-overlapping effects. Graded exposure to such a drug causes graded perturbations to the several cellular states originating at the target proteins.

6. EXAMPLES

The invention having been described, the following examples are offered by way of illustration and not limitation.

6.1. Experimental Protocol

The following experimental methods were used for all the examples. Specific experimental design is described by the examples and their accompanying figures. The specific protocol was also described in Marton et al., 1998, *Drug Target Validation And Identification of Secondary Drug Target Effects Using DNA Microarrays*, NATURE-MEDICINE 4:1293–301.

Transcript Measurement

Yeast (*Saccharomyces cerevisiae*, Strain YPH499, see, Sikorski and Hieter, 1989, A system of shuttle vectors and yeast host strains designated for efficient manipulation of DNA in *Saccharomyces cerevisiae*, Genetics 122:19–27) cells were grown in YAPD at 30° C. to an $OD_{600}$ of 1.0 (±0.2), and total RNA prepared by breaking cells in phenol/chloroform and 0.1 % SDS by standard procedures (Ausubel et al., 1995, Current Protocols in Molecular Biology, Greene Publishing and Wiley-Interscience, New York, Ch. 13). Poly(A)⁺ RNA was selected by affinity chromatography on oligo-dT cellulose (New England Biolabs) essentially as described in Sambrook et al. (Molecular Cloning—A Laboratory Manual (2nd Ed.), Vol. 1, Cold Spring Harbor Laboratory, Cold Spring Harbor, N.Y., 1989). First strand cDNA synthesis was carried out with 2 µg poly(A)⁺ RNA and SuperScript™ II reverse transcriptase (Gibco-BRL) according to the manufacturer's instructions with the following modifications. Deoxyribonucleotides were present at the following concentrations: dA, dG, and dC at 500 µM each, dT at 100 µM and either Cy3-dUTP or Cy5-dUTP (Amersham) at 100 µM. cDNA synthesis reactions were carried out at 42–44° C. for 90 minutes, after which RNA was degraded by the addition of 2 units of RNAse H, and the cDNA products were purified by two successive rounds of centrifugation dialysis using MICROCON-30 microconcentrators (Amicon) according to the manufacturer's recommendations.

Double-stranded DNA polynucleotides corresponding in sequence to each ORF in the *S. cerevisiae* genome encoding a polypeptide greater than 99 amino acids (based on the published yeast genomic sequence, e.g., Goffeau et al., 1996, *Science* 274:546–567) are made by polymerase chain reaction (PCR) amplification of yeast genomic DNA. Two PCR primers were chosen internal to each of the ORFs according to two criteria: (i) the amplified fragments are 300–800 bp and (ii) none of the fragments have a section of more than 10 consecutive nucleotides of sequence in common. Computer programs are used to aid in the design of the PCR primers. Amplification was carried out in 96 well microtitre plates. The resulting DNA fragments were printed onto glass microscope slides using the method of Shalon et al., 1996, *Genome Research* 6:639–645.

Fluorescently-labeled cDNAs (2–6 $\mu$g) are resuspended in 4×SSC plus 1 $\mu$g/$\mu$l tRNA as carrier and filtered using 0.45 $\mu$M filters (Millipore, Bedford, Mass.). SDS is added to 0.3%, prior to heating to 100° C. for 2 minutes. Probes were cooled and immediately hybridized to the microarrays produced as described in Example 6.2, for 4 hours at 65° C. Non-hybridized probe is removed by washing in 1×SSC plus 0.1 % SDS at ambient temperature for 1–2 minutes. Microarrays were scanned with a fluorescence laser-scanning device as previously described (Schena et al., 1995, *Science* 270:467–470; Schena et al., 1995, *Proc. Natl. Acad. Sci. USA* 93:10539–11286) and the results (including the positions of perturbations) are recorded.

6.2. EXAMPLE 1
Overlapping Effect

Figure 3:
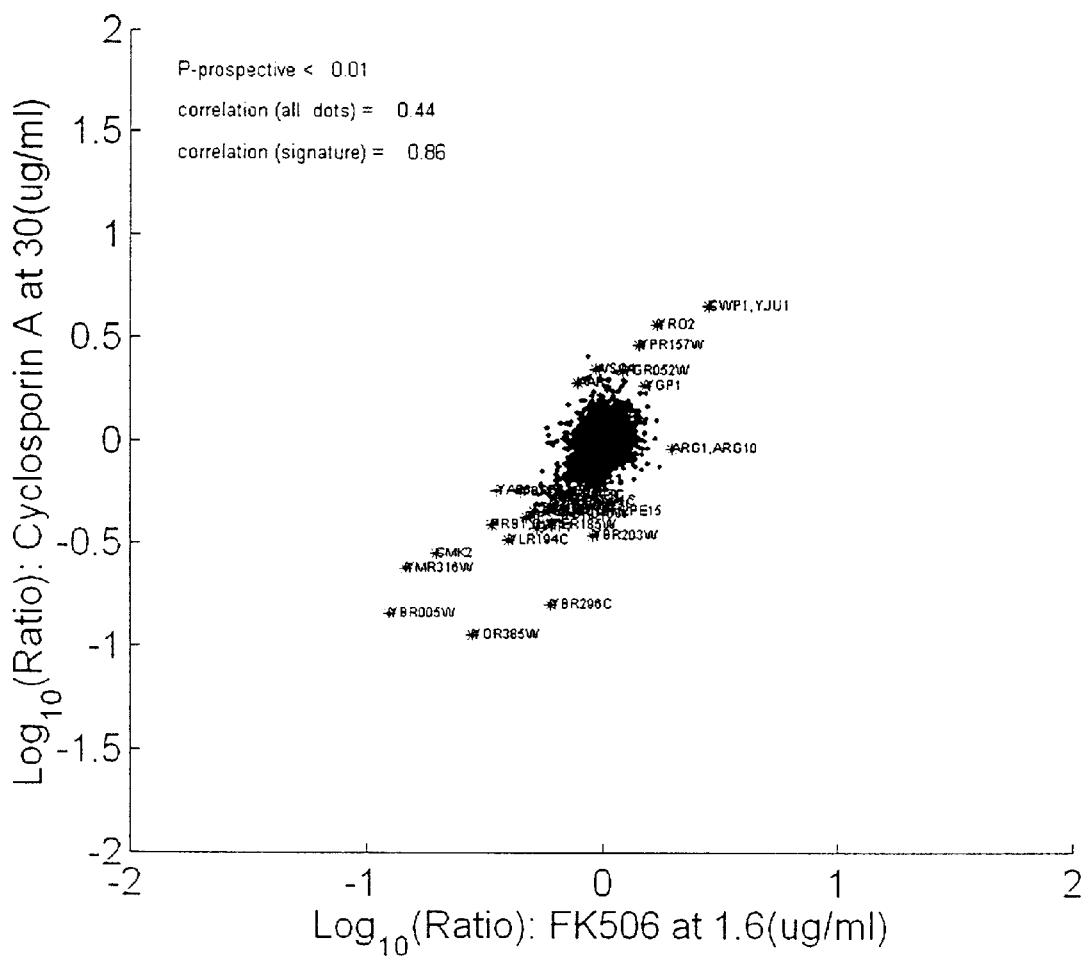
FIG. 3 shows overlapping interaction between FK506 and cyclosporin A (CSA).

Yeast (YPH499) cultures were treated with cyclosporin A, FK506 or clotinmazole. The response profiles for the two immunosuppressant drugs FK506 (1.6 $\mu$g/ml) and Cyclosporin A (30 $\mu$g/ml) is shown in FIG. 3. The axes in FIG. 2 are log 10 (abundance ratio). The two coordinates of each gene were determined by its fold abundance change in response to the two drugs. There is a high degree of commonality in the two profiles as evidenced by the correlation in the scatter plot. The correlation coefficient in this case is 0.86 based on the genes with significant up and down regulations at the 95% confidence level. Genes were labeled with their names and displayed as asterisks if they were up or down regulated in either experiment with at least 95% confidence. The similarity of the responses suggests that simultaneous treatment with FK506 and Cyclosporin A will result in more complete inhibition of the calcineurin protein (their common target) than either treatment alone.

Figure 4:
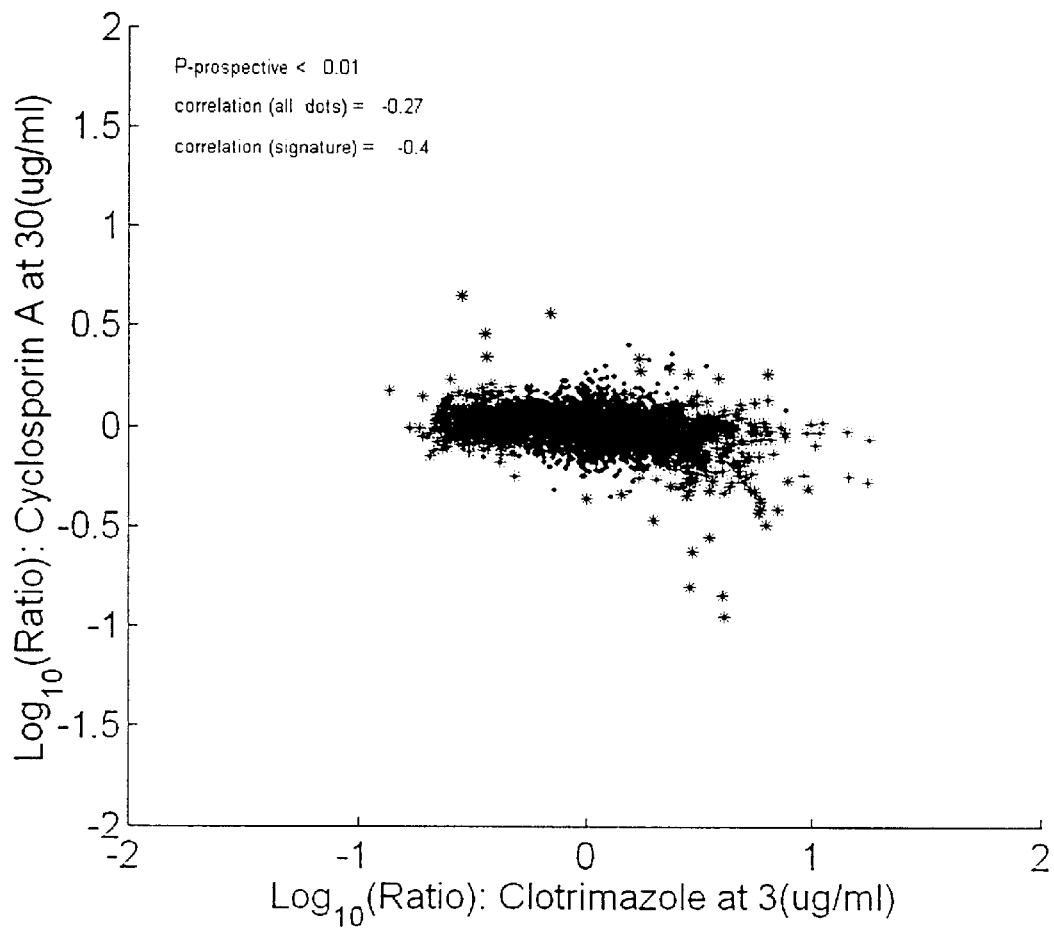
FIG. 4 shows overlapping interaction between cyclosporin A and Clotrimazole.

FIG. 4 is an example of overlap where the effects are of opposite sign for Clotrimazole and Cyclosporin A. Here the anti-correlation of the profiles suggests that simultaneous treatment would result in partial cancellation of the effects of either treatment alone. In FIG. 3, there are a large number of genes that are up or down regulated significantly by Clotrimazole, but whose responses to Cyclosporin are not individually significant. These appear as a horizontal band, and are displayed with gray symbols.

6.3. EXAMPLE 2
Non-additive Overlapping Effect

Figure 5:
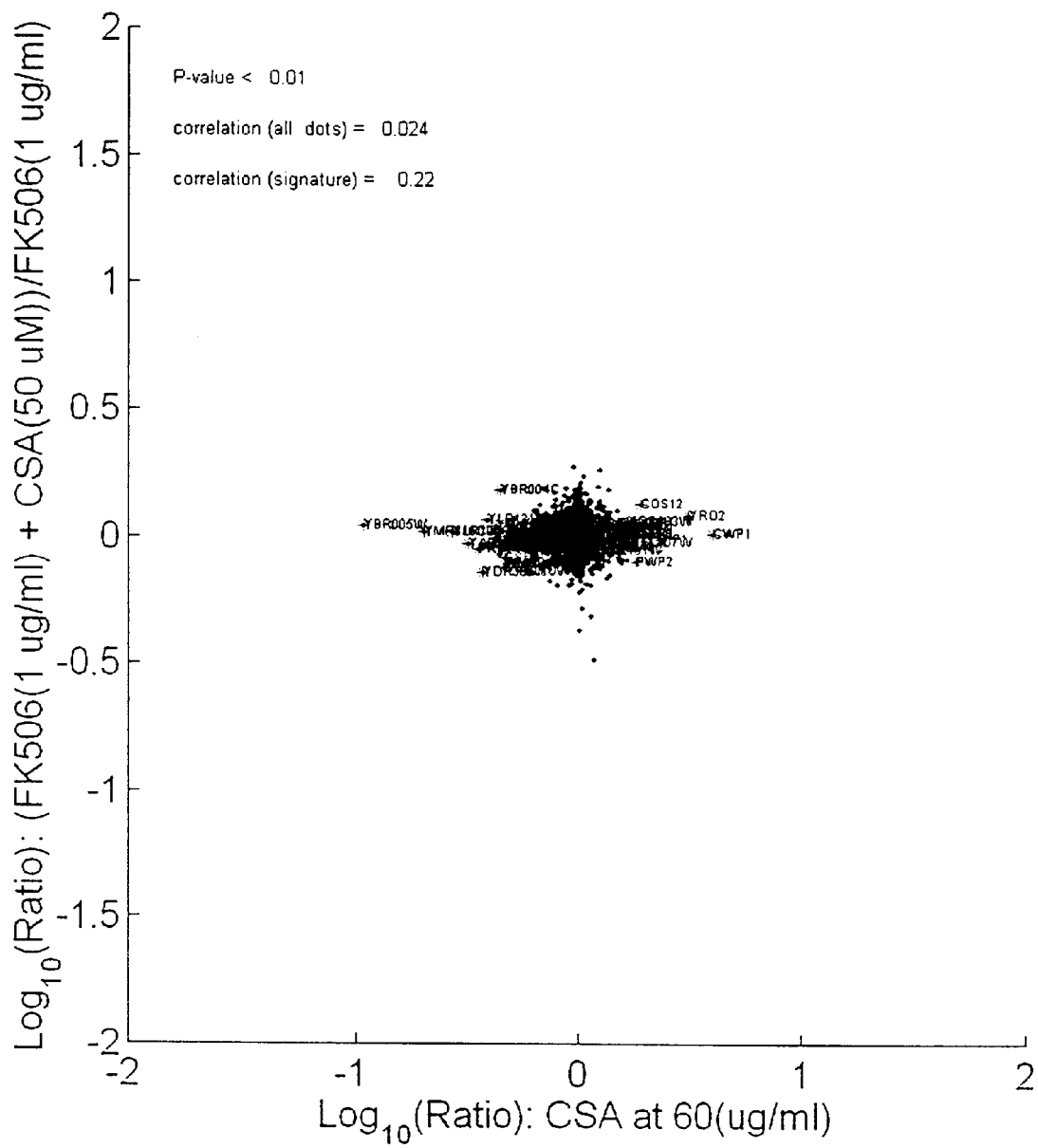
FIG. 5 shows the effect of CSA on gene expression in the presence of FK506

Treatment with Cyclosporin A was compared with treatment with a combination of Cyclosporin A and FK506 (FIG. 5). These two drugs were shown to have overlapping effects in FIG. 3 (Example 1, supra). In FIG. 5, the vertical axis is the response when FK506 is added to a cell containing Cyclosporin. The lack of response along this axis indicates that the Cyclosporin responses, involving the calcineurin pathway, were already saturated by the Cyclosporin treatment. The re-enforcement of the calcineurin inhibition by the FK506 did not produce significant additional response. This absence of response to the added FK506 both confirms the coincidence of the activities of CsA and FK506 and shows that the cell was already in a state of saturated response along the affected pathway.

6.4. EXAMPLE 3
Detection of Interaction Effects

Figure 6:
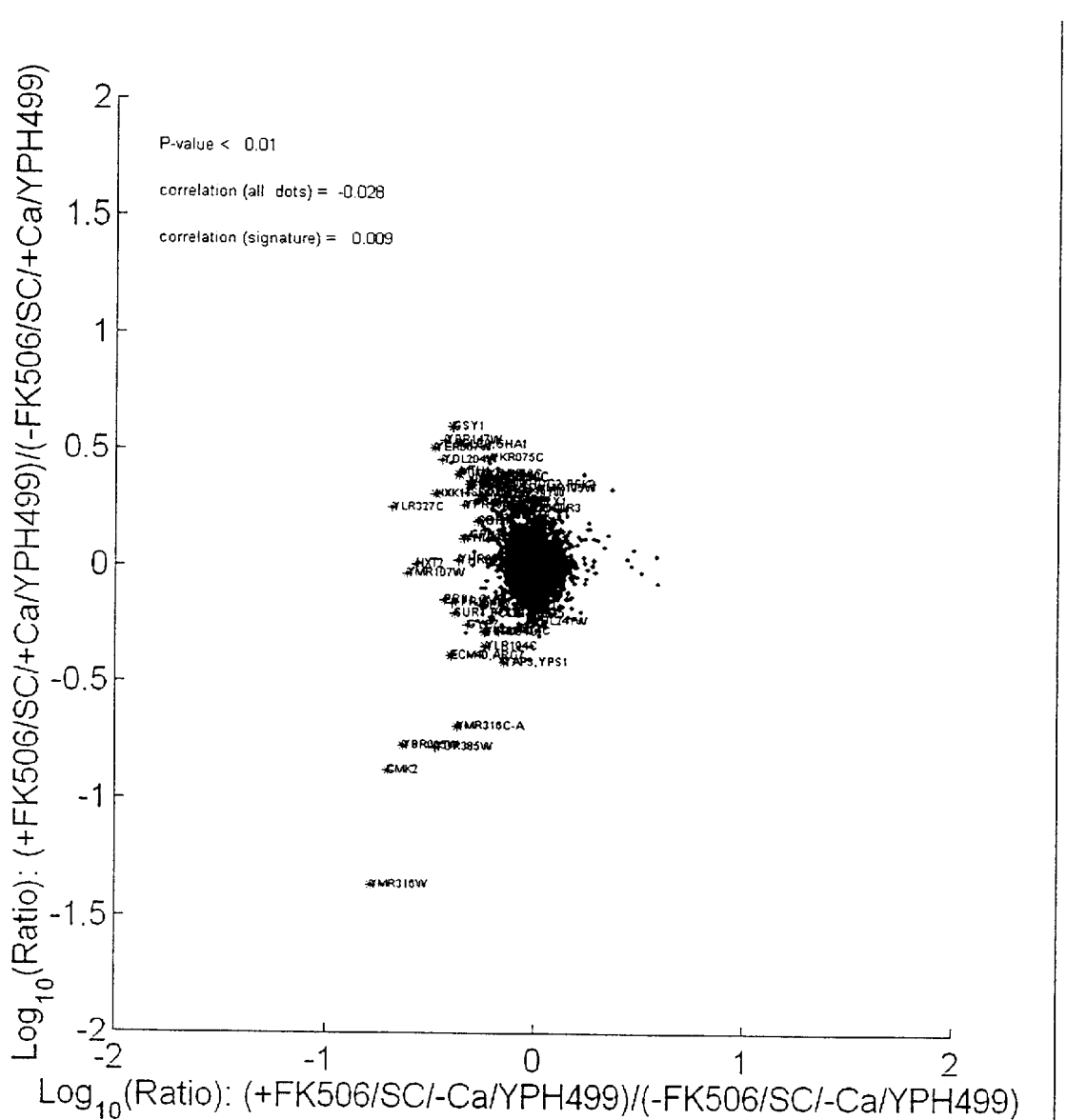
FIG. 6 shows the effect of calcium on gene expression in the presence of FK506.

This example illustrates the method for detecting nonlinear interaction between drugs. The following two condition pairs were tested in yeast cultures. Condition Pair 1: baseline strain grown in calcium poor medium vs. strain with genetic deletion of calcineurin gene grown in calcium poor medium. Condition Pair 2: baseline strain grown in calcium rich medium vs. strain with calcineurin deletion grown in calcium rich medium FIG. 6 gives the scatter plot of the response profile of Condition Pair 1 vs. Condition Pair 2. There are many genes which lie along the line x=y (the 45° line) indicating that most of the effects of adding Calcium do not depend on the existence of Calcineurin. However, there are also several genes in the upper left quadrant, which probably constitute interaction effects. In FIG. 6, only those genes whose regulations are significant at the 95% confidence level in one or both experiments are flagged with the gene names.

6.5. EXAMPLE 4
No Interaction

Figure 7:
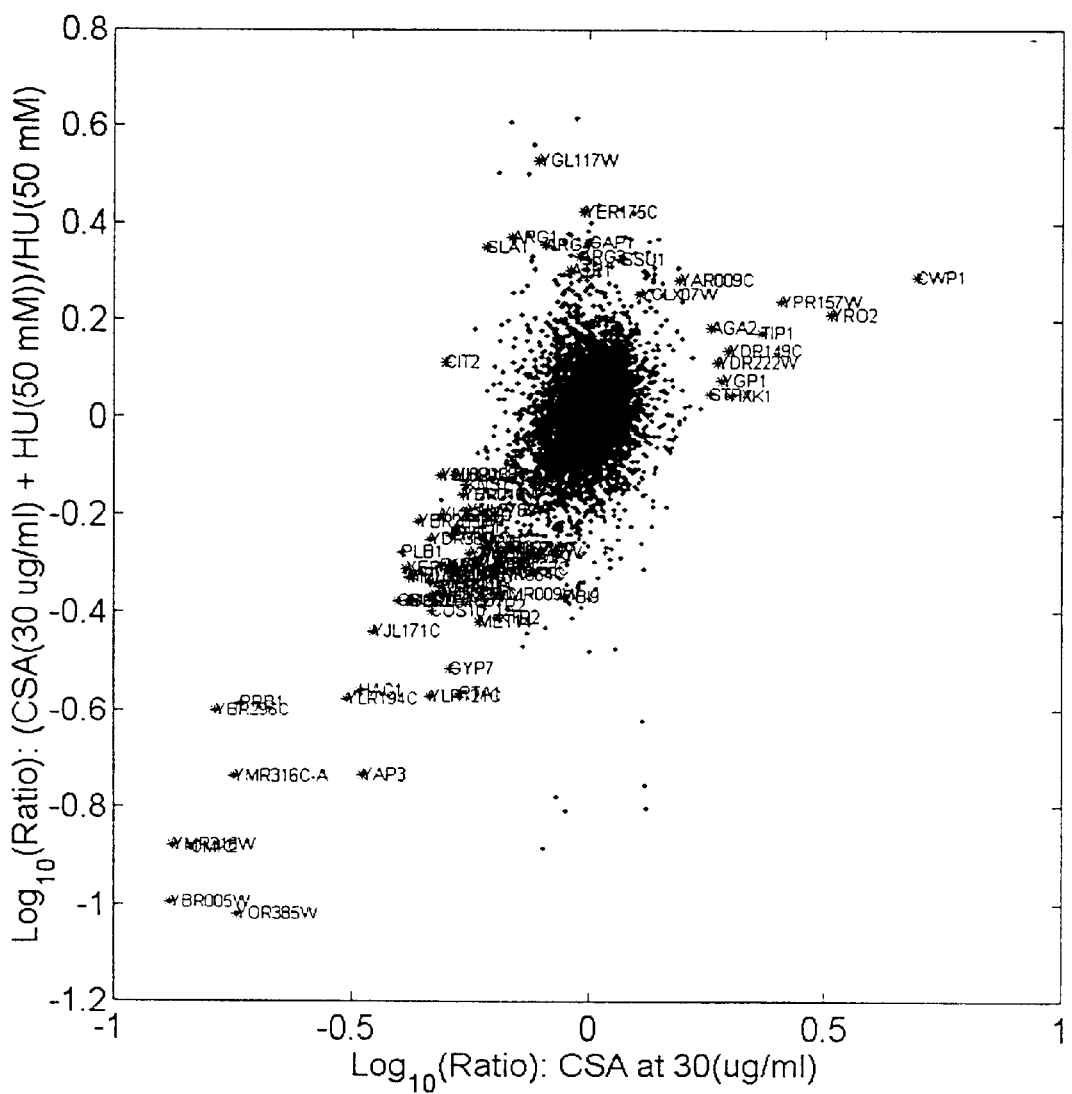
FIG. 7 shows the effect of hydroxyurea (hu) in the presence of CSA.

A yeast culture was treated with Cyclosporin A as one experiment, and simultaneous treatment with Cyclosporin A and hydroxyurea as the other experiment, shown in FIG. 7. Here the Cyclosporin effects appear to be independent of hydroxyurea, since there is a high correlation between the horizontal and vertical coordinates in the scatter plot. Most of the genes which appear in the region just above the main ball of points are members of the hydroxyurea signature, suggesting that the effects of hydroxyurea were not balanced in the condition pair used to generate the vertical coordinate in FIG. 7. This can occur if there are minor inconsistencies in the way the two cultures were handled, such as slight differences in the time of drug treatment.

7. References Cited

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for predicting the likelihood of an interaction between two different perturbations, comprising:

calculating a correlation coefficient between a first and a second response profile, wherein said first response profile comprises measurements of a plurality of cellular constituents in a first sample of a cell, tissue, organ or multicellular organism in response to a first perturbation, and said second response profile comprises measurements of said plurality of cellular constituents in a second sample of said cell, tissue, organ or multicellular organism in response to a second perturbation different from said first perturbation; and predicting the likelihood of an interaction between said first perturbation and said second perturbation based on said correlation coefficient; wherein said interaction is the alteration of the effects of said second perturbation by said first perturbation or the alteration of the effects of said first perturbation by said second perturbation, and wherein a high possibility of interaction is predicted if said correlation coefficient is high.

2. The method of claim 1 wherein said cellular constituents are within a target pathway of said first perturbation and said second perturbation.

3. The method of claim 1 wherein said cellular constituents are transcripts of a plurality of genes.

4. The method of claim 1 wherein said first sample and said second sample are yeast cultures.

5. A method for predicting the likelihood of an interaction between two different perturbations, comprising:

analyzing extent of correlation or overlap between a first and a second response profile, wherein said first response profile comprises measurements of a plurality of cellular constituents consisting of at least 5 different cellular constituents in a first sample of a cell, tissue, organ or multicellular organism in response to a first perturbation, and said second response profile comprises measurements of said plurality of cellular constituents in a second sample of said cell, tissue, organ or multicellular organism in response to a second perturbation different from said first perturbation; and predicting the likelihood of an interaction between said first perturbation and said second perturbation based on said extent of correlation or overlap; wherein said interaction is the alteration of the effects of said second perturbation by said first perturbation or the alteration of the effects of said first perturbation by said second perturbation, and a high possibility of interaction is predicted if a substantial correlation or overlap occurs between said first response profile and said second response profile.

6. A method for predicting the likelihood of an interaction between two different perturbations, comprising:

analyzing extent of correlation or overlap between a first and a second response profile, wherein said first response profile comprises measurements of a plurality of cellular constituents in a first sample of a cell, tissue, organ or multicellular organism in response to a first perturbation, and said second response profile comprises measurements of said plurality of cellular constituents in a second sample of said cell, tissue, organ or multicellular organism in response to a second perturbation different from said first perturbation, wherein said cellular constituents are within a target pathway of said first perturbation and said second perturbation; and predicting the likelihood of an interaction between said first perturbation and said second perturbation based on said extent of correlation or overlap; wherein said interaction is the alteration of the effects of said second perturbation by said first perturbation or the alteration of the effects of said first perturbation by said second perturbation, and a high possibility of interaction is predicted if a substantial correlation or overlap occurs between said first response profile and said second response profile.

7. A method for predicting the likelihood of an interaction between two different perturbations, comprising:

analyzing extent of correlation or overlap between a first and a second response profile, wherein said first response profile comprises measurements of a plurality of cellular constituents in a first sample of a cell, tissue, organ or multicellular organism in response to a first perturbation, and said second response profile comprises measurements of said plurality of cellular constituents in a second sample of said cell, tissue, organ or multicellular organism in response to a second perturbation different from said first perturbation, wherein said cellular constituents are transcripts of a plurality of genes; and predicting the likelihood of an interaction between said first perturbation and said second perturbation based on said extent of correlation or overlap; wherein said interaction is the alteration of the effects of said second perturbation by said first perturbation or the alteration of the effects of said first perturbation by said second perturbation, and a high possibility of interaction is predicted if a substantial correlation or overlap occurs between said first response profile and said second response profile.

8. A method for predicting the likelihood of an interaction between two different perturbations, comprising:

analyzing extent of correlation or overlap between a first and a second response profile, wherein said first response profile comprises measurements of a plurality of cellular constituents in a first sample of a yeast culture in response to a first perturbation, and said second response profile comprises measurements of said plurality of cellular constituents in a second sample of said yeast culture in response to a second perturbation different from said first perturbation; and predicting the likelihood of an interaction between said first perturbation and said second perturbation based on said extent of correlation or overlap; wherein said interaction is the alteration of the effects of said second perturbation by said first perturbation or the alteration of the effects of said first perturbation by said second perturbation, wherein a high possibility of interaction is predicted if a substantial correlation or overlap occurs between said first response profile and said second response profile.

9. The method of claim 5 wherein said first perturbation is a first drug and said second perturbation is a second drug.

10. A method for predicting the likelihood of an interaction between two different perturbations, comprising:

analyzing extent of correlation or overlap between a first and a second response profile, wherein said first response profile comprises measurements of a plurality of cellular constituents in a first sample of a cell, tissue, organ or multicellular organism in response to a first perturbation, wherein said first perturbation is a first disease risk factor, and said second response profile comprises measurements of said plurality of cellular constituents in a second sample of said cell, tissue, organ or multicellular organism in response to a second perturbation different from said first perturbation, wherein said second perturbation is a second disease risk factor; and predicting the likelihood of an interaction between said first perturbation and said second perturbation based on said extent of correlation or overlap; wherein said interaction is the alteration of the effects of said second perturbation by said first perturbation or the alteration of the effects of said first perturbation by said second perturbation, wherein a high possibility of interaction is indicated if a substantial correlation or overlap occurs between said first response profile and said second response profile.

11. A method of analyzing interaction between a first perturbation and second perturbation different from said first perturbation, comprising:

analyzing relationship between a first response profile ($R_A$) and a second response profile ($R_{A|B}$), wherein said first response profile ($R_A$) comprises measurements of responses of a plurality of cellular constituents to a first perturbation when said second perturbation is absent and said second response profile ($R_{A|B}$) comprises measurements of responses of said plurality of cellular constituents to said first perturbation when said second perturbation is present, wherein said relationship indicates said interaction, said interaction being the alteration of the effects of said second perturbation by said first perturbation or the alteration of the effects of said first perturbation by said second perturbation, and wherein said step of analyzing comprises plotting said first profile ($R_A$) against second profile ($R_{A|B}$) in a plot, wherein response of each of said cellular constituents is a data point; a horizontal axis represents response to said first perturbation when said second perturbation is absent and a vertical axis represents response to said first perturbation when said second perturbation is present.

12. The method of claim 11 wherein said step of analyzing comprises determining which different regions of said plot said cellular constituents fall into.

13. The method of claim 12 wherein said step of analyzing further comprises indicating that said first perturbation acts on a cellular constituent independently of said second perturbation if said cellular constituent falls in a region along the 45° line.

14. The method of claim 13 wherein said step of analyzing further comprises indicating that the activity of said first perturbation on a cellular constituent is enhanced or reduced by said second perturbation if said cellular constituent falls within the upper right or lower left quadrants, but not in a region along the 45° line.

15. The method of claim 12 wherein said step of analyzing further comprises indicating that the activity of said first perturbation on a cellular constituent is dependent upon said second perturbation if said cellular constituent falls within the lower right or upper left quadrant.

16. The method of claim 12 wherein said step of analyzing further comprises indicating that the activity of said first perturbation is enhanced or reduced by said second perturbation if a significant number of said cellular constituents fall within the upper right or lower left quadrants, but not in a region along the 45° line.

17. The method of claim 12 wherein said analyzing step further comprises indicating that the activity of said first perturbation is dependent upon said second perturbation if a significant number of said cellular constituents fall within the lower right or upper left quadrant.

18. The method of claim 11 wherein said step of analyzing further comprises assigning cellular constituents in different regions of said plot with an objective statistical significance.

19. The method of claim 13, 14, 15, 16 or 17 wherein said cellular constituents are transcripts of a plurality of genes.

20. The method of claim 13, 14, 15, 16 or 17 wherein said cellular constituents are of a yeast culture.

21. The method of claim 13, 14, 15, 16 or 17 wherein said first perturbation is a first drug and second perturbation is a second drug.

22. The method of claim 13, 14, 15, 16 or 17 wherein said first perturbation is a plurality of drugs.

23. The method of claim 13, 14, 15, 16 or 17 wherein said second perturbation is a plurality of drugs.

24. The method of claim 13, 14, 15, 16 or 17 wherein said first perturbation is a first disease risk factor and said second perturbation is a second disease risk factor.

25. A method of analyzing interaction between a perturbation A and a perturbation B, comprising: calculating interaction effect vector {I} according to:

$$\{I\} = \{R_{A,B}\} - (\{R_A\} + \{R_B\})$$

wherein said vector $\{R_A\}$ represents a set of cellular constituents with threshold crossing response when subject to said perturbation A but not perturbation B; said vector $\{R_B\}$ represents a set of cellular constituents with threshold crossing response when subject to said perturbation B but not said perturbation A; and said vector $\{R_{A,B}\}$ is a set of cellular constituents with threshold crossing response when subject to both said perturbation A and perturbation B, wherein said interaction effect vector {I} indicates said interaction; said interaction being the alteration of the effects of perturbation B by perturbation A or the alteration of the effects of perturbation A by perturbation B, and wherein said cellular constituents are transcripts of a plurality of genes.

26. The method of claim 25 wherein said threshold is two-fold induction or reduction.

27. The method of claim 26 wherein said perturbation A is a first drug and said perturbation B is a second drug.

28. The method of claim 26 wherein said perturbation A is a plurality of drugs.

29. The method of claim 26 wherein said perturbation B is a plurality of drugs.

30. The method of claim 26 wherein said perturbation A is a first disease risk factor and said perturbation B is a second disease risk factor.

31. A method of comparing a plurality of interactions, comprising:
a) analyzing each of said interactions by a method comprising i) plotting a first response profile ($R_A$) against a second response profile ($R_{A|B}$) in a plot, wherein said first response profile ($R_A$) comprises measurements of responses of a plurality of cellular constituents to a first perturbation when said second perturbation is absent and said second response profile ($R_{A|B}$) comprises measurements of responses of said plurality of cellular constituents to said first perturbation when said second perturbation is present, and wherein response of each of said cellular constituents is a data point in said plot; a horizontal axis represents response to said first perturbation when said second perturbation is absent and a vertical axis represents response to said first perturbation when said second perturbation is present; and ii) determining which different regions of said plot said cellular constituents fall into; wherein each of said interactions is between two perturbations; and
b) ranking the severity of said interactions by the number of said cellular constituents found to be significantly in upper left or lower right, or by number significantly away from the 45° line, thereby comparing said plurality of interactions; wherein each said interaction is the alteration of the effects of said second perturbation by said first perturbation or the alteration of the effects of said first perturbation by said second perturbation.

32. The method of claim 31 wherein said perturbations are different drugs.

33. The method of claim 32 wherein said perturbations are different disease risk factors.

34. A method for predicting the likelihood of an interaction between two different perturbations, comprising:
analyzing extent of correlation or overlap between a first and a second response profile, wherein said first response profile comprises measurements of a plurality of cellular constituents consisting of at least 5 different cellular constituents in a first sample of a cell, tissue, organ or multicellular organism in response to a first perturbation, and said second response profile comprises measurements of said plurality of cellular constituents in a second sample of said cell, tissue, organ or multicellular organism in response to a second perturbation different from said first perturbation; and predicting the likelihood of an interaction between said first perturbation and said second perturbation based on said extent of correlation or overlap; wherein said interaction is the alteration of the effects of said second perturbation by said first perturbation or the alteration of the effects of said first perturbation by said second perturbation, and a high possibility of interaction is predicted if a substantial correlation or overlap occurs between said first response profile and said second response profile.

35. The method of claim 34 wherein said plurality of cellular constituents consists of at least 10 different cellular constituents.

36. The method of claim 35 wherein said plurality of cellular constituents consists of at least 100 different cellular constituents.

37. The method of claim 18 wherein said step of assigning is based upon a 95% or greater confidence.

38. A method of analyzing interaction between a first perturbation and second perturbation different from said first perturbation, comprising:

analyzing relationship between a first response profile ($R_A$) and a second response profile ($R_{A|B}$), wherein said first response profile ($R_A$) comprises measurements of responses of a plurality of cellular constituents to a first perturbation when said second perturbation is absent and said second response profile ($R_{A|B}$) comprises measurements of responses of said plurality of cellular constituents to said first perturbation when said second perturbation is present, wherein said relationship indicates said interaction, said interaction being the alteration of the effects of said second perturbation by said first perturbation or the alteration of the effects of said first perturbation by said second perturbation, and wherein said plurality of cellular constituents consists of at least 5 different cellular constituents.

39. The method of claim 38 wherein said plurality of cellular constituents consists of at least 10 different cellular constituents.

40. The method of claim 39 wherein said plurality of cellular constituents consists of at least 100 different cellular constituents.

41. A method of analyzing interaction between a perturbation A and a perturbation B, comprising: calculating interaction effect vector $\{I\}$ according to:

$$\{I\} = \{R_{A,B}\} - (\{R_A\} + \{R_B\})$$

wherein said vector $\{R_A\}$ represents a set of cellular constituents with threshold crossing response when subject to said perturbation A but not perturbation B; said vector $\{R_B\}$ represents a set of cellular constituents with threshold crossing response when subject to said perturbation B but not said perturbation A; and said vector $\{R_{A,B}\}$ is a set of cellular constituents with threshold crossing response when subject to both said perturbation A and perturbation B, wherein said interaction effect vector $\{I\}$ indicates said interaction; said interaction being the alteration of the effects of perturbation B by perturbation A or the alteration of the effects of perturbation A by perturbation B, and wherein each of said $\{R_A\}$, $\{R_B\}$, and $\{R_{A,B}\}$ consists of responses of at least 5 different cellular constituents.

42. The method of claim 41 wherein each of said $\{R_A\}$, $\{R_B\}$, and $\{R_{A,B}\}$ consists of responses of at least 10 different cellular constituents.

43. The method of claim 42 wherein each of said $\{R_A\}$, $\{R_B\}$, and $\{R_{A,B}\}$ consists of responses of at least 100 different cellular constituents.

44. The method of any one of claim 38–43, wherein said cellular constituents are transcripts of a plurality of genes.

* * * * *